(12) United States Patent
Staub et al.

(10) Patent No.: US 12,186,529 B2
(45) Date of Patent: Jan. 7, 2025

(54) DRUG DELIVERY DEVICE

(71) Applicant: SOCIETE INDUSTRIELLE DE SONCEBOZ SA, Sonceboz (CH)

(72) Inventors: David Staub, Courtelevant (FR); Thierry Martin, Mont de Vougney (FR); Nicolas Bailo, Nidau (CH); Denis Tilloy, Sonceboz (CH)

(73) Assignee: SOCIETE INDUSTRIELLE DE SONCEBOZ SA, Sonceboz (CH)

(*) Notice: Subject to any disclaimer, the term of this patent is extended or adjusted under 35 U.S.C. 154(b) by 223 days.

(21) Appl. No.: 17/581,315

(22) Filed: Jan. 21, 2022

(65) Prior Publication Data

US 2022/0143311 A1    May 12, 2022

Related U.S. Application Data

(62) Division of application No. 16/482,213, filed as application No. PCT/EP2018/052179 on Jan. 29, 2018, now Pat. No. 11,413,392.

(30) Foreign Application Priority Data

Jan. 31, 2017 (EP) .................................. 17153997

(51) Int. Cl.
 *A61M 5/142*   (2006.01)
 *A61M 5/14*   (2006.01)
 (Continued)

(52) U.S. Cl.
CPC ...... *A61M 5/14248* (2013.01); *A61M 5/1409* (2013.01); *A61M 5/14216* (2013.01);
(Continued)

(58) Field of Classification Search
CPC ........ F04B 3/00; F04B 7/0015; F04B 7/0053; F04B 7/0225; F04B 7/045; F04B 9/025;
(Continued)

(56) References Cited

U.S. PATENT DOCUMENTS 3,464,359 A * 9/1969 Johnson ................ A61M 5/142
  604/152
5,673,689 A * 10/1997 Power ............... A61M 16/0057
  128/203.12

(Continued)

FOREIGN PATENT DOCUMENTS

EP   2992916 A1   3/2016
EP   3050585 A1   8/2016
(Continued)

OTHER PUBLICATIONS

International Preliminary Report on Patentability received for PCT Patent Application No. PCT/EP2018/052179, mailed on Aug. 15, 2019, 15 pages.

(Continued)

*Primary Examiner* — James D Ponton
(74) *Attorney, Agent, or Firm* — Faegre Drinker Biddle & Reath LLP

(57) ABSTRACT

There is described a patch pump comprising a cartridge, a power source, a pump system, a drug delivery device and a control system configured to operate in particular the pump system and the drug delivery device. The pump system includes, on the one hand, a pump having a pump housing containing a pump piston and a valve piston and, on the other hand, a pump drive including a piston motor and a valve motor for driving the pump piston and the valve piston independently from each other through a first and a second transmission. The drug delivery device includes a transdermal delivery system having a needle actuation mechanism configured for transdermal insertion of a cannula.

11 Claims, 13 Drawing Sheets

(51) Int. Cl.
　　　*A61M 5/145*　　(2006.01)
　　　*A61M 5/158*　　(2006.01)
　　　*A61M 5/168*　　(2006.01)
　　　*F04B 7/04*　　(2006.01)
(52) U.S. Cl.
　　　CPC ...... *A61M 5/1454* (2013.01); *A61M 5/16809* (2013.01); *A61M 5/16827* (2013.01); *A61M 2005/14252* (2013.01); *A61M 2005/14506* (2013.01); *A61M 2005/14533* (2013.01); *A61M 2005/1585* (2013.01); *A61M 2005/1588* (2013.01); *F04B 7/045* (2013.01)
(58) Field of Classification Search
　　　CPC .......... F04B 7/04; F04B 9/02; F04B 53/1092; F04B 3/003; A61M 5/145; A61M 5/1452; A61M 5/1456; A61M 5/20; A61M 5/31; A61M 5/315; A61M 5/31576; A61M 5/31596; A61M 37/00; A61M 2005/3114; A61M 2037/0007; A61M 5/14248; A61M 5/1409; A61M 5/14216; A61M 5/1454; A61M 5/16809; A61M 5/16827; A61M 2005/14252; A61M 2005/14506; A61M 2005/14533; A61M 2005/1585; A61M 2005/1588; A61M 2005/1583; A61M 2039/224; A61M 25/0606; A61M 5/1422; A61M 5/3287
　　　See application file for complete search history.

(56) References Cited

U.S. PATENT DOCUMENTS

| | | |
|---|---|---|
| 7,846,132 B2 | 12/2010 | Gravesen et al. |
| 2014/0058353 A1 | 2/2014 | Politis et al. |
| 2016/0213851 A1* | 7/2016 | Weibel ............... A61B 5/14532 |
| 2019/0365993 A1 | 12/2019 | Staub et al. |

FOREIGN PATENT DOCUMENTS

| | | |
|---|---|---|
| GB | 0757116 | 9/1956 |
| WO | 2008/024810 A2 | 2/2008 |
| WO | 2008/133702 A1 | 11/2008 |
| WO | 2011/133823 A1 | 10/2011 |
| WO | 2012/108955 A2 | 8/2012 |
| WO | 2014/090745 A1 | 6/2014 |
| WO | 2014/191038 A1 | 12/2014 |
| WO | 2015/032747 A1 | 3/2015 |

OTHER PUBLICATIONS

International Search Report and Written Opinion issued by the European Patent Office, mailed Jul. 24, 2018, for International Patent Application No. PCT/EP2018/052179; 25 pages.

\* cited by examiner

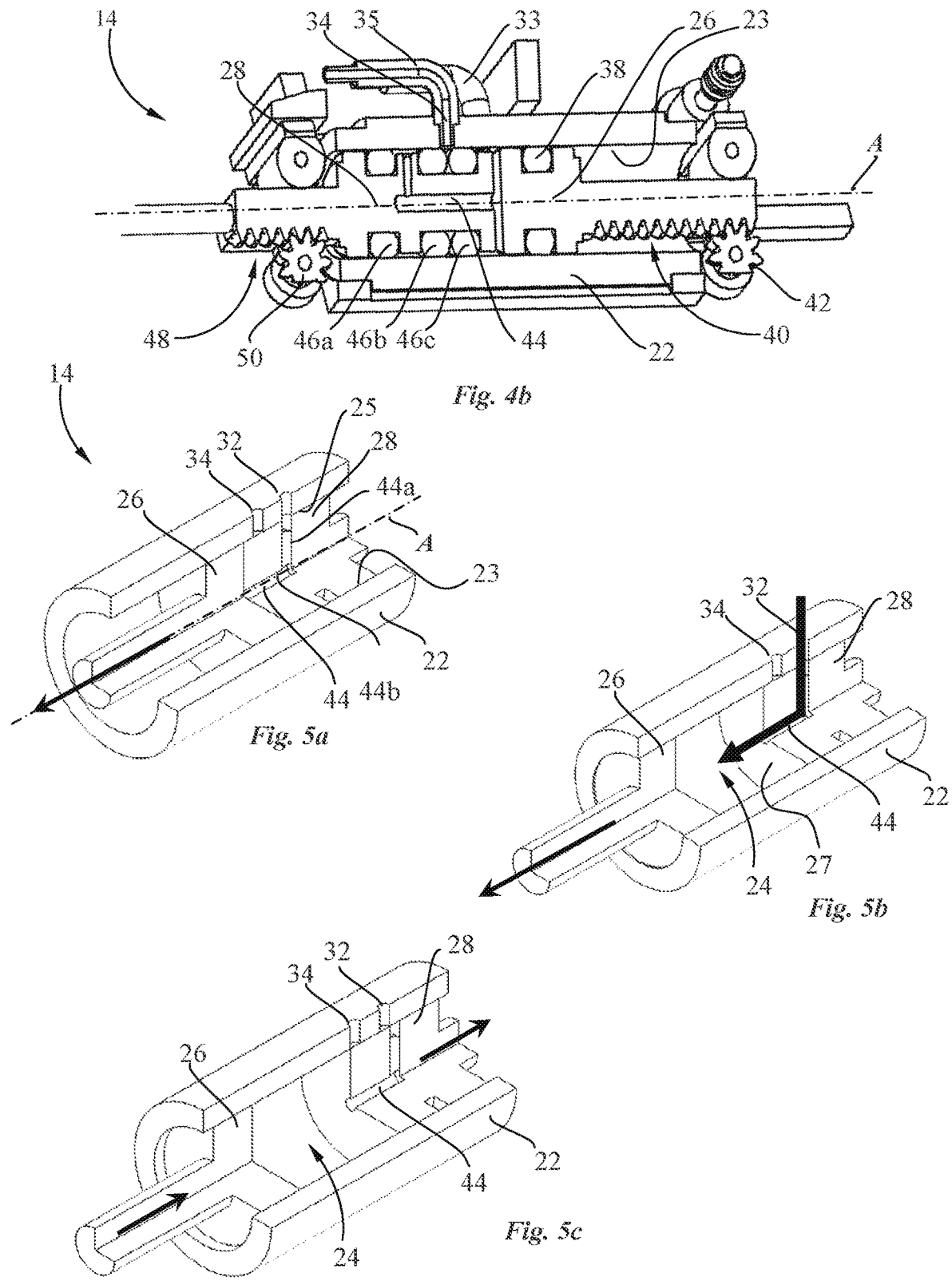

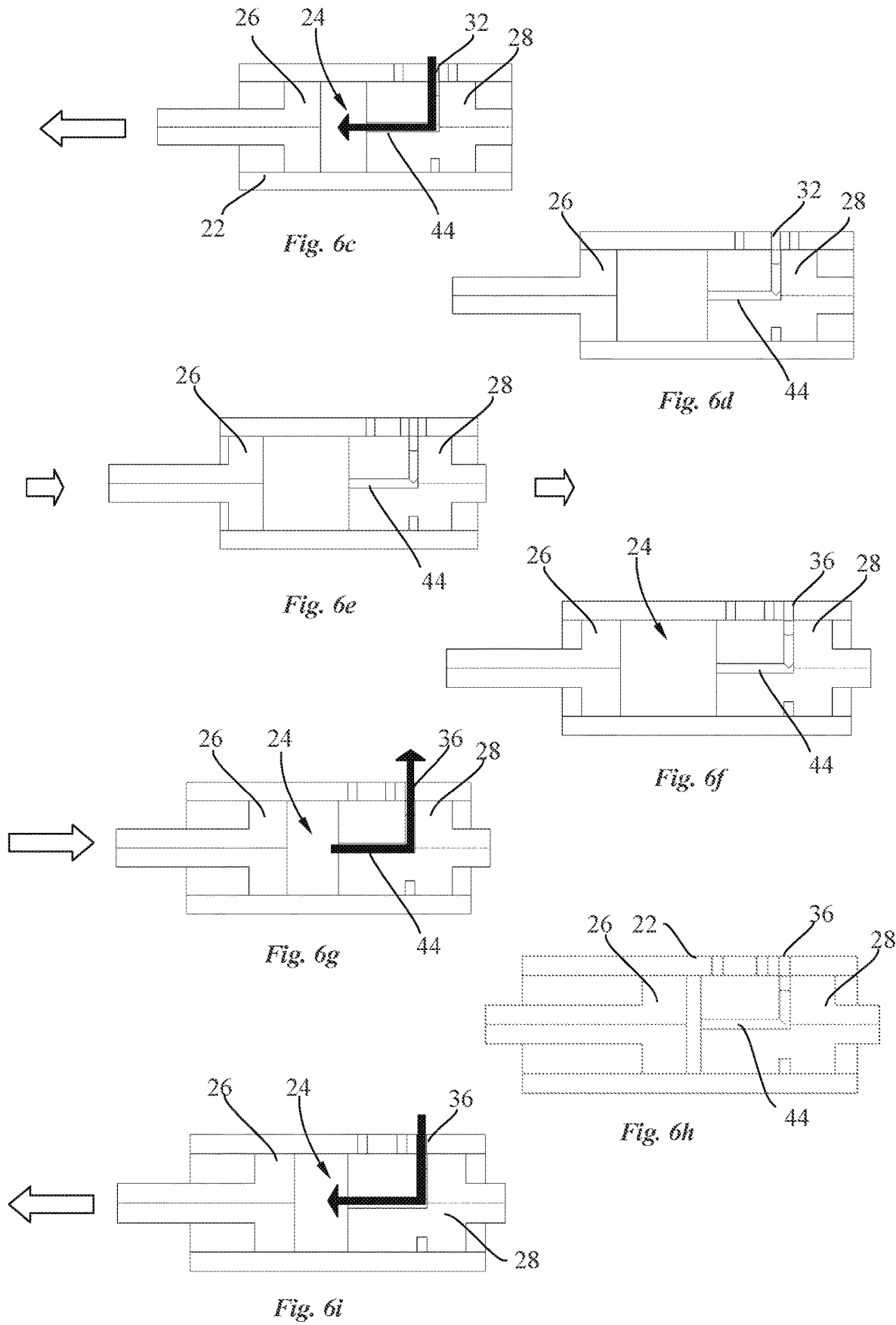

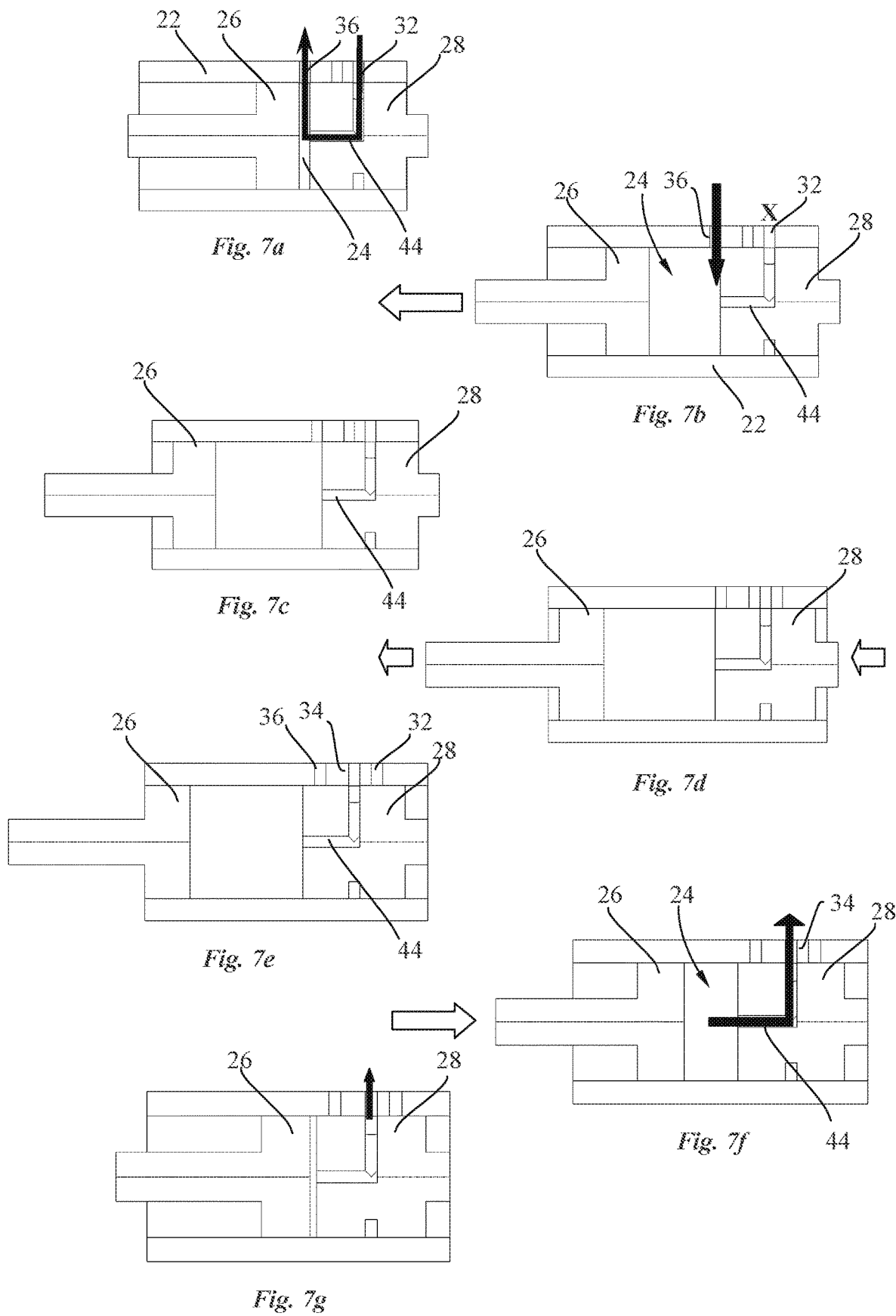

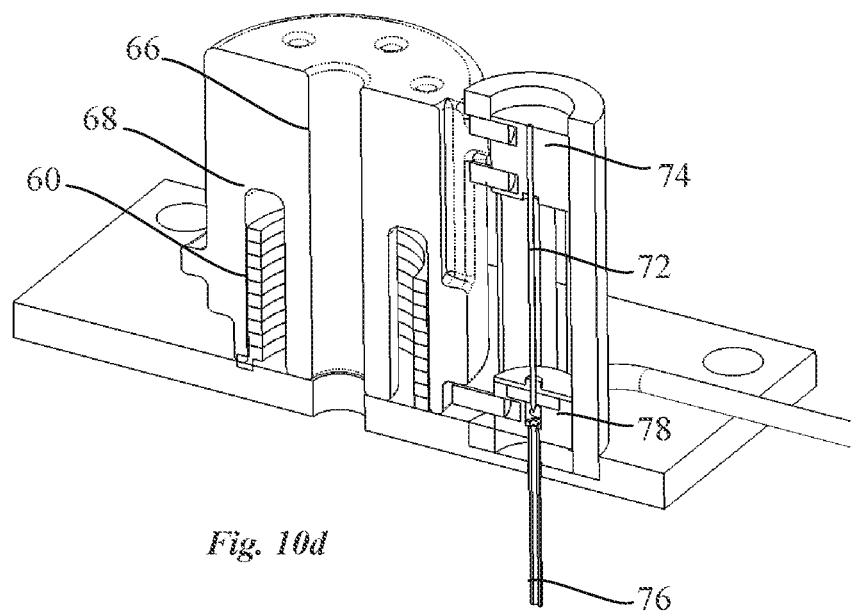
*Fig. 10d*
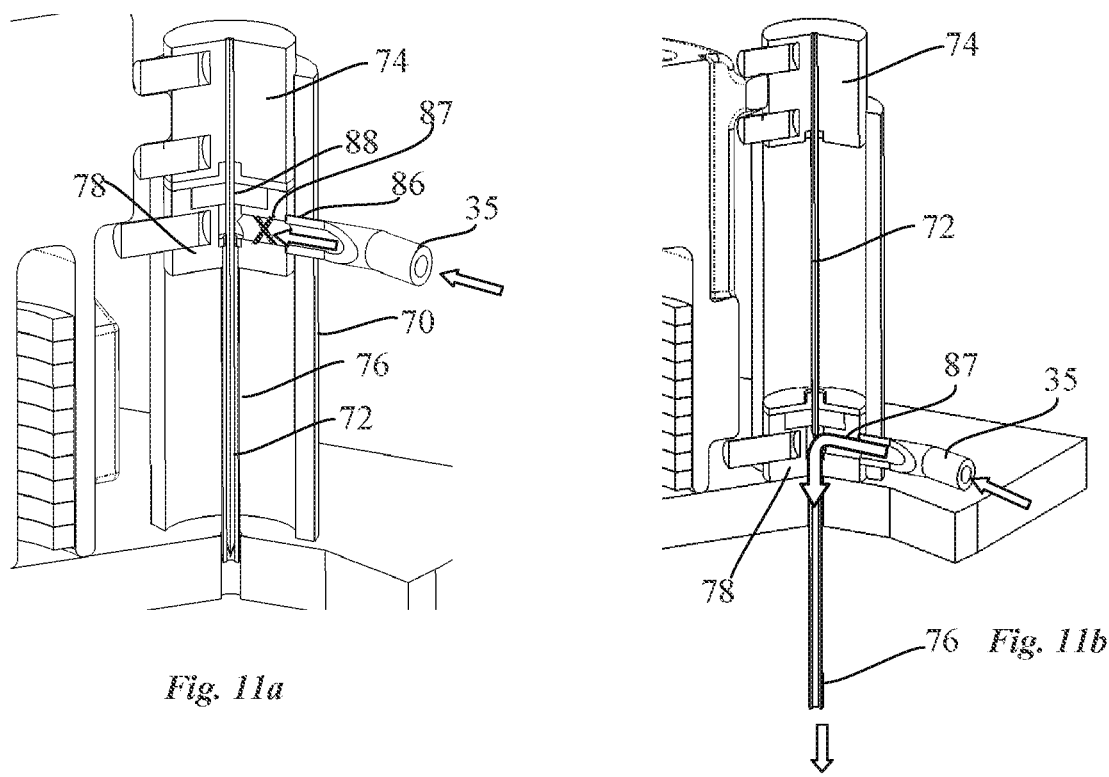
*Fig. 11a*   *Fig. 11b*

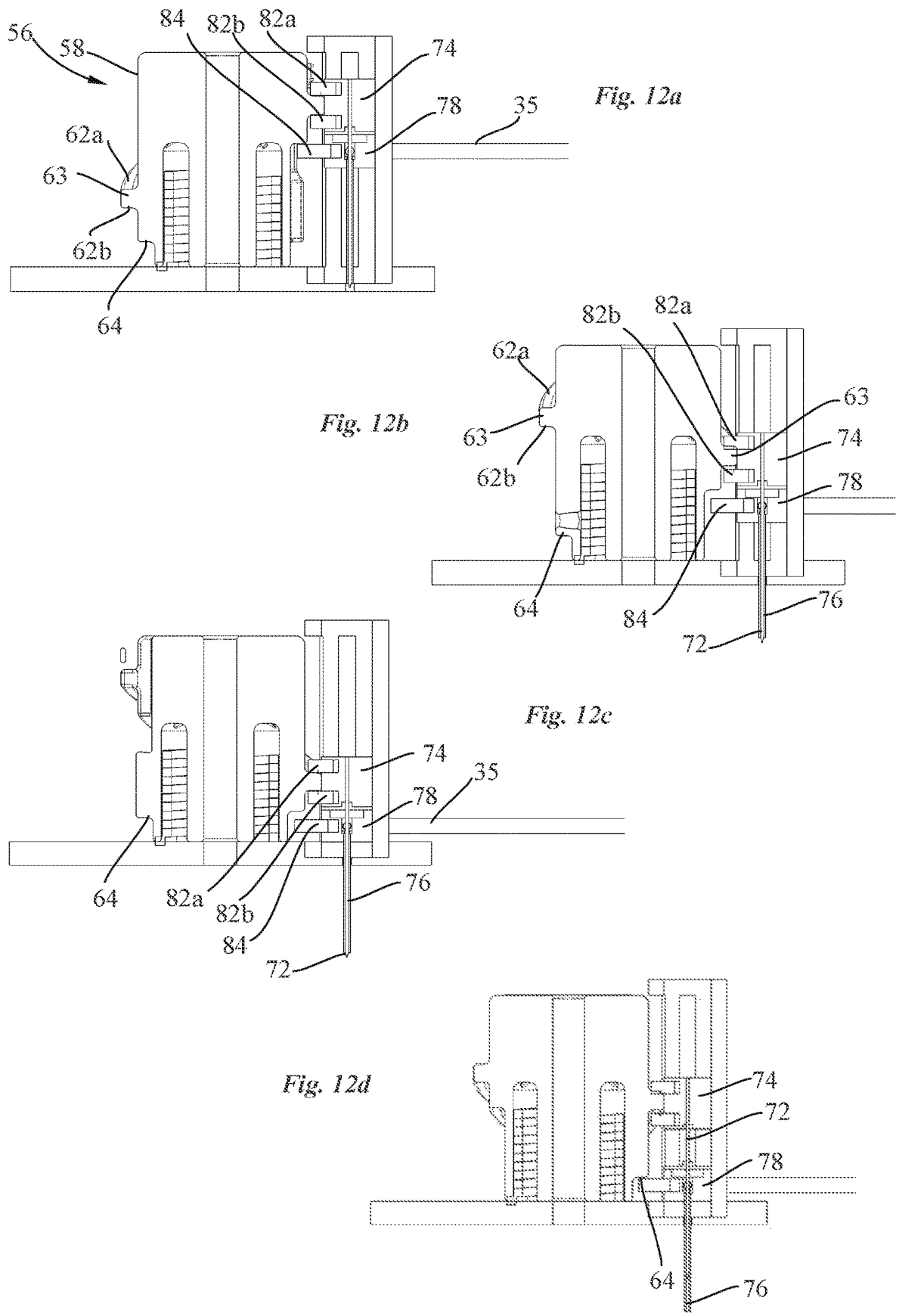

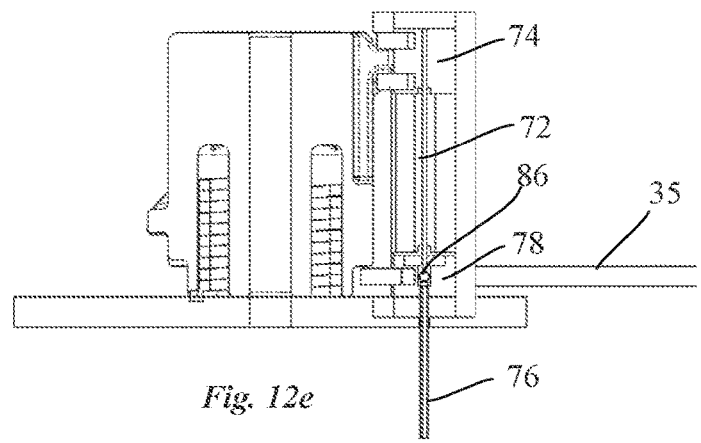
*Fig. 12e*
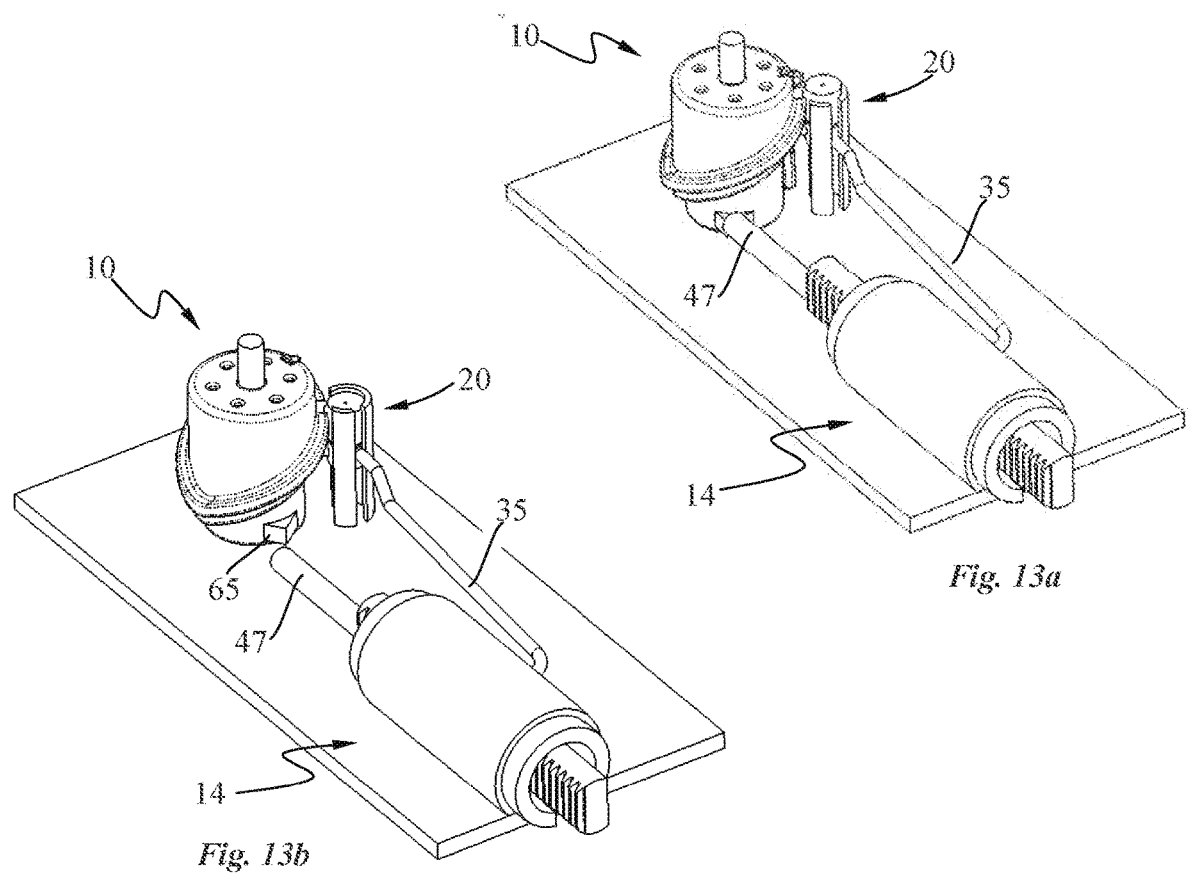
*Fig. 13a*
*Fig. 13b*

DRUG DELIVERY DEVICE

CROSS-REFERENCE TO RELATED APPLICATIONS

The present application is a divisional of U.S. patent application Ser. No. 16/482,213, filed Jul. 30, 2019, which is a national stage entry of International (PCT) Patent Application Number PCT/EP2018/052179, filed Jan. 29, 2018, which in turn claims priority to European Patent Application No. 17153997.6, filed Jan. 31, 2017, the subject matter of which are expressly incorporated herein by reference.

TECHNICAL FIELD

The present invention relates to a drug delivery device for transdermal delivering a medicament. The drug delivery device may in particular be in the form of a patch pump for drug delivery incorporating a pump system and a transdermal delivery system.

DESCRIPTION OF RELATED ART

The regular trans-dermal administration of doses of a medicament is necessary in the control or therapy of many conditions, such as diabetes, growth hormone deficiency, pain therapy, and treatment after chemotherapy. For instance, diabetic patients may require injections of insulin several times a-day. The insulin dosage regime required for a diabetic patient varies depending on a number of factors including, for instance, the type of diabetes, the type of insulin administered, the actual severity of the condition, the lifestyle of the patient, the routine and diet of the patient. Accordingly diabetic patients often need to administer doses of insulin themselves, several times a day, and in places other than hospitals or medical centres.

A number of drug delivery devices have been developed to facilitate the self-administration of medicaments. These devices are generally in the form of a patch pump integrating a cartridge containing a drug to be administered, a micropump for pumping a predetermined volume of the drug from the cartridge and a transcutaneous delivery system comprising a needle actuation mechanism for transcutaneous insertion of a cannula for delivering the drug to a patient.

Examples of needle actuation mechanisms for transcutaneous insertion of a cannula are given in WO2008/024810 and U.S. Pat. No. 7,846,132. The mechanisms have separate biasing elements to effect the needle insertion movement and the needle withdrawal movement, which may have an adverse impact on the reliability of such mechanisms. Moreover, using a septum according to WO2008/024810 configured to be pierced to bring a reservoir of a drug delivery device in fluid communication with the cannula increases the risk of contamination and the difficulty of ensuring sterile conditions.

One example of a micropump developed to be easily integrated into a patch pump is given in EP2992916. This pump is adapted for continuous delivery of a liquid medication such as insulin for treatments of diabetes and comprises a piston provided with a rack engaging a pinion gear of a motor and is mounted to move back and forth inside a floating piston which remains fixed by frictional engagement with the internal surface of the pump housing. The floating piston comprises a channel configured to bring in fluid communication the piston chamber with the inlet and outlet of the pump housing when the torque produced by the motor overcomes the frictional engagement of the floating piston. A drawback of this system includes the non-optimal ratio between the pumped volume and the pump size. Also, the pumped volume is invariable and defined by the fixed piston stroke, whereby for certain applications, it would be desirable to be able to vary the pumped volume.

An object of the invention, according to a first aspect, is to provide a drug delivery device with a transdermal delivery system that is reliable, safe and comfortable for a patient.

It would be advantageous to provide a transdermal delivery system configured to work with a thin needle and cannula gauge.

It would be advantageous to provide a transdermal delivery system that provides safe fluid connection between a reservoir and a cannula.

It would be advantageous to provide a transdermal delivery system that is cost-effective to manufacture.

It would be advantageous to provide a transdermal delivery system that is easy to operate and use.

It would be advantageous to provide a transdermal delivery system compatible with the injection of both standard and high viscosity drugs.

An object of the invention, according to another aspect, is to provide a pump system for medical applications that is reliable, versatile, and compact.

It would be advantageous to provide a pump system that is cost-effective to manufacture.

It would be advantageous to provide a pump system that is accurate, in particular for pumping small volumes.

It would be advantageous to provide a pump system with low energy consumption.

It would be advantageous to provide a pump system that can be used for different medical applications.

It would be advantageous to be able to pump liquids with different properties, in particular with different viscosities, and in varying volumes.

An object of the invention, according to a third aspect, is to provide a drug reconstitution device that is reliable, in particular that enables a good reconstitution of a drug, in a compact configuration.

It would advantageous to provide a drug reconstitution device that is versatile, in particular that can be used for different medical applications or that is able to reconstitute liquids with different properties, in particular with different viscosities, and in varying volumes.

It would be advantageous to provide a drug reconstitution device that is cost-effective to manufacture.

It would be advantageous to provide a drug reconstitution device that is easy to operate and use.

It would be advantageous to provide a drug reconstitution device that is power efficient.

SUMMARY OF THE INVENTION

Objects of the invention are achieved by a transdermal delivery system of a drug delivery device according to claim 1.

Disclosed herein, according to a first aspect of the invention, is a drug delivery device comprising a transdermal delivery system having a needle actuation mechanism configured for transdermal insertion of a cannula and a needle guiding element for guiding axial displacement of a needle and a cannula. The needle actuation mechanism comprises a cam member having a cam housing and a spring housed inside the cam housing in order to impart rotational movement to the cam member relative to the needle guiding element. The guiding element guides a needle fixed to a needle holder and a cannula fixed to a cannula holder. The needle and cannula holders comprise each an engagement portion, wherein the engagement portion of the needle holder is configured to engage with a first and a second cam surface and the engagement portion of the cannula holder is configured to engage with a locking surface. The first and second cam surfaces are arranged around the circumference of an outer surface of the cam housing along a first portion with a first gradient configured for the needle insertion movement followed by a second portion with a second gradient configured for the needle retraction movement such that the needle and the cannula are moved from a retracted position to an extended position upon rotation of the cam member through a first predetermined angle, and such that the needle is brought back in the retracted position upon further rotation of said cam member through a second predetermined angle, whereby during rotation through said second predetermined angle, the engagement portion of the cannula holder abuts against the locking surface to maintain the cannula in the extended position.

In an embodiment, the first and second cam surface may advantageously correspond to each side of a needle holder guide disposed around the circumference of the cam member along a first gradient portion configured for the needle insertion movement followed by a second gradient portion configured for the needle retraction movement.

The needle holder guide may for instance be a projecting part or a groove.

In an embodiment, the cam member may advantageously comprise a cam housing containing a spring element configured to impart angular movement to the cam member so as to provide a self-driven cam member.

In an embodiment, in a position prior to use, the cam member may engage with a cam engaging element to prevent rotation of the cam member.

The delivery system may advantageously further comprise a needle insertion release mechanism configured to disengage the cam engaging element to enable rotation of the cam member caused by the spring element.

In an embodiment, the needle guiding element comprises a needle housing for sliding movement of the needle and cannula holders inside the needle housing. A shape of the transversal cross-section of the housing may correspond to a shape of the transversal cross-section of the needle and cannula holders.

In an embodiment, the needle holder may advantageously be mounted on top of the cannula holder and cooperates with the needle guiding element to ensure axial displacement of the needle and the cannula upon rotation of the cam member, wherein the cannula holder comprises a through hole for receiving the needle.

In an embodiment, the cannula holder may comprise an inlet aperture for receiving an inlet tube, and an inlet channel extending from the inlet aperture to the through hole. The needle may advantageously be adapted to perform the function of sealing between the inlet channel and the cannula to avoid any leakage prior to use of the delivery system.

In an embodiment, the inlet aperture of the cannula holder may advantageously be configured to be in fluid communication with the cannula once the needle is moved back in the retracted position after actuation of the needle actuation mechanism of the transcutaneous delivery system.

Also disclosed herein, according to a second aspect of the invention, is a drug delivery device including a transcutaneous delivery system comprising a needle actuation mechanism configured for transcutaneous insertion of a needle, and a needle guiding element for axial displacement of a needle. The needle actuation mechanism comprises a cam member rotatable relative to the needle guiding element about an axis distant from the needle axis. The cam member comprises a cam housing containing a biased element configured to impart angular movement to the cam member. The guiding element contains a needle connected to a needle holder. The needle holder comprises an engagement portion configured to engage with a first and a second cam surface of a needle holder guide disposed around the circumference of the cam housing along a first portion with a negative gradient followed by a second portion with a positive gradient such that the needle are moved between a retracted position and an extended position upon rotation of the cam member through a predetermined angle of rotation and such that the needle is brought back in the retracted position upon further rotation of the cam member.

In an advantageous embodiment, rotation of the cam housing is stopped by a locking element when the needle has reached the extended position. Upon completion of the drug injection, a needle insertion release mechanism disengages the locking element from the cam housing to enable further rotation of the cam housing to safely move the needle in the retracted position, thereby avoiding needle injury.

Objects of the invention are achieved by a pump system of a drug delivery device according to claim 10.

Disclosed herein, according to a third aspect of the invention, is a pump system for a drug delivery device, comprising a pump drive and a pump. The pump comprises a pump housing having inlet and outlet ports and forming a pump chamber containing a pump piston and a valve piston. The pump comprises a valve channel configured to selectively connect and disconnect at least one of the inlet and outlet ports of the pump housing to the pump chamber as a function of the position of the valve piston. The pump piston and the valve piston are linearly slidable along a common axis (A) within the pump chamber, and wherein the valve piston and pump piston are independently actuated.

In an advantageous embodiment, the pump drive comprises a valve motor coupled to the valve piston and a piston motor coupled to the pump piston, the valve and piston motors being independently controllable.

In an embodiment, the pump drive comprises a first transmission coupling the valve motor to the valve piston, and a second transmission coupling the pump motor to the pump piston.

In an advantageous embodiment, each of the first and second transmissions comprises a toothed rack fixed to the respective piston, and a reduction gear assembly between the respective motor and toothed rack.

The pump drive may be configured to linearly actuate the valve piston without any angular movement.

In an embodiment, the valve piston may be a single piece sealingly fitted inside the pump housing. The valve channel may be configured to extend from the inner surface of the pump housing, through the valve piston, into the pump chamber of the pump.

In an advantageous embodiment, the pump system the valve piston comprises an over-molded part comprising a valve channel portion configured to engage the inner surface of the pump housing so as to form with said inner surface the valve channel.

In an advantageous embodiment, the over-molded part is configured to selectively seal the inlet and outlet ports from the pump chamber.

Also disclosed herein, according to a fourth aspect of the invention, is a drug reconstitution device including a pump system as described above according to the third aspect, whereby the pump housing comprises an additional port, the additional port and the inlet port corresponding to first and second drug reconstitution ports. The drug reconstitution device is configured for coupling a first constituent container containing a first constituent and a second constituent container containing a second constituent, wherein the outlet port of the pump housing is configured to deliver the reconstituted drug comprising the first and second constituents.

In an advantageous embodiment, the drug reconstitution device further comprises a docking interface comprising a first and a second container docking interface configured to interconnect the first and second constituent containers respectively with the first and second drug reconstitution ports of the pump housing in a fluidic manner.

In an advantageous embodiment, the over-molded part of the valve piston is configured to selectively seal the first and second drug reconstitution ports and the outlet port from the pump chamber.

In an advantageous embodiment, the valve piston of the pump of the drug reconstitution device may be formed in a single piece with overmolded sealing parts such that the valve piston is sealingly fitted inside the pump housing.

In an advantageous embodiment, the valve channel of the valve piston of the pump of the drug reconstitution device may be configured to extend from the inner surface of the pump housing, through the valve piston, into the pump chamber.

Also disclosed herein, according to a fifth aspect of the invention, is a method for reconstituting a drug using a pump system comprising a pump drive and a pump having a pump housing comprising first and second drug reconstitution ports and an outlet port. The pump housing forms a pump chamber containing a pump piston and a valve piston, wherein the pump comprises a valve channel configured to selectively connect and disconnect at least one of the first and second reconstitution ports to the pump chamber as a function of the position of the valve piston and wherein the pump piston and the valve piston are linearly slidable along a pump axis (A) within the pump chamber, and wherein the valve piston and pump piston are independently actuated.

The method may comprise the following steps: i.) setting the valve piston in a first axial position in which the drug reconstitution ports of the pump housing are in fluid communication; ii.) urging a first constituent contained in a first container through the valve channel of the pump into a second container containing substance second constituent in order to reconstitute the drug inside the second container during a drug reconstitution phase; iii.) driving the pump piston away from the valve piston along the pump axis to draw the reconstituted drug from the second container into the pump chamber during a chamber filling phase; iv.) driving the valve piston in a second axial position, upon completion of the chamber filling phase, in which the valve channel is aligned with the outlet port while the drug reconstitution ports are closed by the valve piston; and v.) driving the pump piston towards the piston valve along the pump axis to expel the reconstituted drug from the pump chamber, through the valve channel and the outlet port during a drug administration phase.

In an embodiment, the diluent or solvent contained in the first container is urged through successively the first drug reconstitution port, the valve channel, the pump chamber, and the second drug reconstitution port into the second container during the drug reconstitution phase.

In an embodiment, the diluent or solvent contained in the first container is urged through successively the second drug reconstitution port, the pump chamber, the valve channel, and the first drug reconstitution port into the second container during the drug reconstitution phase.

In an advantageous embodiment, the valve piston may be set in a safety position, prior to step i.) in which the drug reconstitution ports and the outlet port of the pump housing are closed by the valve piston.

In an embodiment, the first container may be pressurized thereby urging the solvent from the first container into the second container during the drug reconstitution phase without having the need to drive the pump system.

In an embodiment, the first container is in the form of a syringe. The solvent may be urged from the syringe to the second container when the plunger of the syringe is pushed to empty the syringe during the drug reconstitution phase.

Also disclosed herein, according to a sixth aspect of the invention, is a patch pump comprising the drug delivery device according to the first aspect of the invention, the pump system according to the third aspect of the invention or the drug reconstitution device according to the fourth aspect of the invention, a cartridge, a power source and a control system.

Various features herein may be combined with one or more of the above aspects to provide combinations other than those specifically illustrated and described. Further objects and advantageous features of the invention will be apparent from the claims, from the detailed description, and annexed drawings.

BRIEF DESCRIPTION OF THE DRAWINGS

For a better understanding of the invention, and to show how embodiments of the same may be carried into effect, reference will now be made, by way of example, to the accompanying drawings in which:

FIG. 4b is a close-up view of the pump of FIG. 4a of the pump system;

FIGS. 5a to 5e are perspective cross-sectional views of a portion of a pump system according to an embodiment of the invention, whereby FIGS. 5a to 5e illustrate different steps of a pumping sequence according to an embodiment of the invention;

FIG. 6a, and FIGS. 6b to 6n, are perspective cross-sectional, respectively plan cross-sectional, views of a portion of a pump system according to another embodiment of the invention for reconstitution of a drug, whereby FIGS. 6b to 6n illustrate different steps of a pumping sequence for drug reconstitution according to an embodiment of the invention;

FIGS. 7a to 7g are cross-sectional views of the portion of the pump system illustrating different steps of a pumping sequence for drug reconstitution according to another embodiment of the invention;

FIG. 10d is a cross-sectional view of the transdermal delivery system of FIG. 10c;

FIGS. 11a and 11b are cross-sectional views of a needle guiding element respectively in a position prior to use and during use according to an embodiment of the invention;

FIGS. 12a to 12e are cross-sectional views of the transdermal delivery system of FIGS. 10a to 10c showing different sequences for transdermally insertion of a cannula according to an embodiment of the invention, and FIGS. 13a and 13b are perspective views of the pump and the transdermal delivery system respectively before and after actuation of a needle insertion release mechanism.

DETAILED DESCRIPTION OF EXEMPLARY EMBODIMENTS

Figure 1:
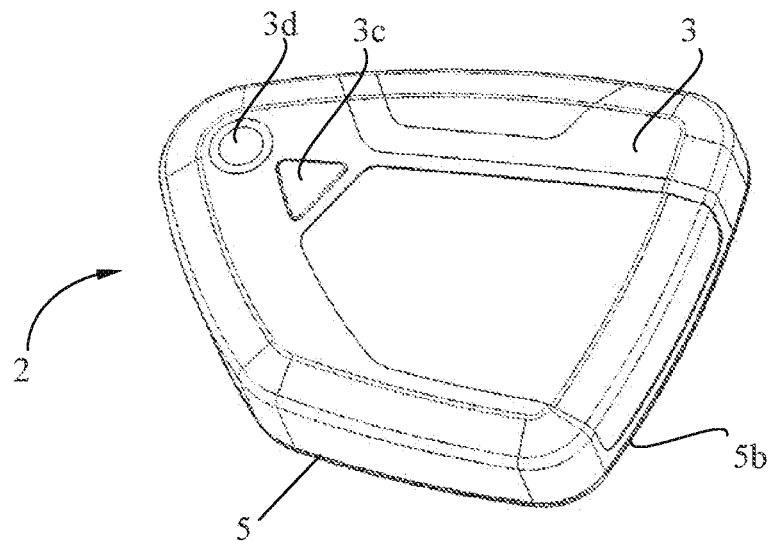
FIG. 1 is a perspective view of a drug delivery device in the form of a patch pump according to an exemplary embodiment of the invention.
Figure 2:
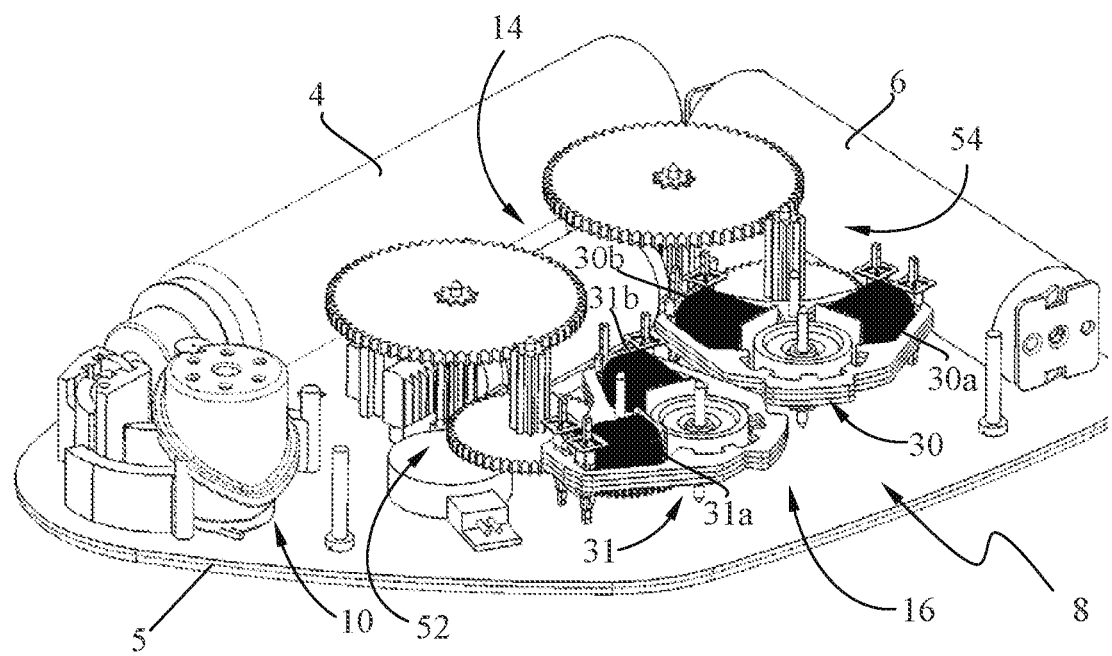
FIG. 2 is a perspective view of a portion of the patch pump of FIG. 1 without cover showing inter alia a pump system, cartridge and power source of the patch pump.
Figure 3:
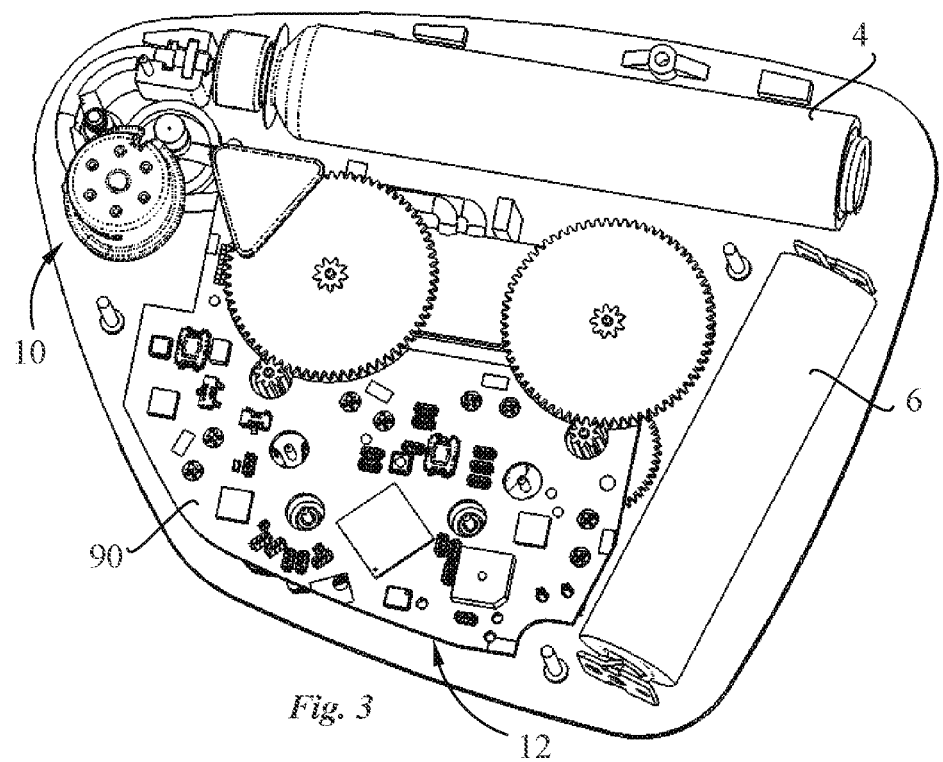
FIG. 3 is another perspective view of a portion of the patch pump of FIG. 1 without cover.
Figure 4A:
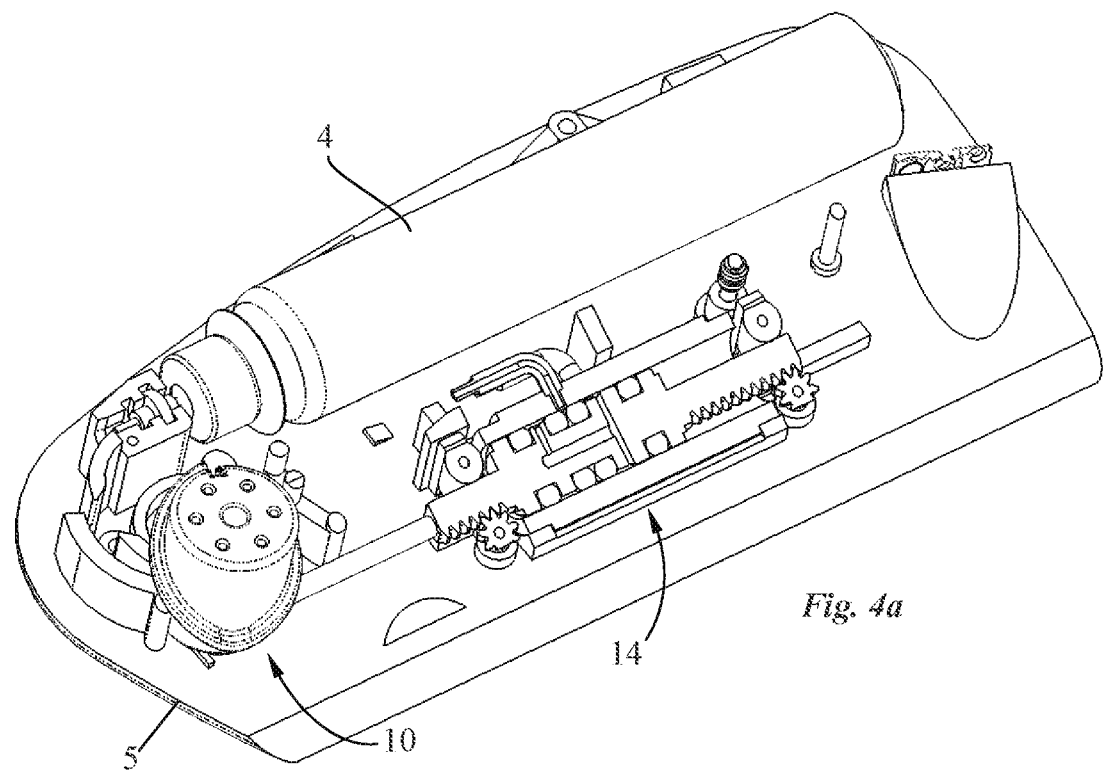
FIG. 4a is a perspective view of a part of the patch pump of FIG. 2, with the pump system comprising a transdermal delivery system and a pump shown in cross-section according to an embodiment of the invention.

Referring to the figures, in particular FIGS. 1-3, a drug delivery device in the form of a patch pump 2 according to an embodiment of the invention, includes a patch pump housing comprising a cover portion 3 and a base 5 defining a skin bonding surface 5b, a cartridge 4 containing a drug to be administered, a power source, for instance in the form of a battery 6, a pump system comprising a pump 14 and a pump drive 16 coupled to the pump via a transmission 52, 54, a transdermal delivery system 10 and a control system 12 (FIG. 3) configured in particular to operate the pump drive 16 of the pump system and to release the transdermal delivery system for transdermally insertion of a cannula as it will be described subsequently. The cover portion 3 comprises an activation button 3c and a status display 3d. The skin bonding surface 5b of the base 5 may be provided with an adhesive layer, per se known in the field, for bonding the patch pump to a patient's skin.

As best seen in FIGS. 4a to 5e, the pump 14 comprises a pump housing 22 provided with inlet and outlet ports 32, 34, a pump chamber 24, a reciprocated pump piston 26 and a valve piston 28 configured to be driven along an axial direction A without any angular movement about the valve axis. The valve piston 28 is sealingly and slidably mounted inside the pump housing 22 and includes a valve channel 44 configured to connect the inlet port 32 with the pump chamber 24 so as to draw fluid from the inlet port 32, through the valve channel 44 into the pump chamber 24 during a chamber filling stroke of the pump piston 26, and to connect the outlet port 34 with the pump chamber 24 so as to expel fluid from the pump chamber 24 through the outlet port 34 during a chamber emptying stroke of the pump piston 26. A shown in particular in FIGS. 5a and 5b, the valve channel 44 of the valve piston 28 comprises a first portion 44a extending from the lateral guide surface 25 of valve piston adjacent the inner surface 23 of the pump housing 22, and a second portion 44b extending to a chamber side face 27 of the valve piston facing the pump chamber 24. Various valve channel shapes, sizes and positions between the lateral guide surface 25 and chamber side surface 27 of the valve piston 28 may be configured.

In the illustrated embodiment, the inlet port 32 is fluidically connected to the cartridge 4 through a first liquid conduit, for instance in the form of a tube 33, while the outlet port 34 is connected to the transdermal delivery system 10 through a second liquid conduit, for instance in the form of a tube 35 (FIGS. 4a and 4b) as will be discussed in more detail hereinafter. However, it may be appreciated that the pump 14 may be used in other medical applications where the inlet and outlet ports 32, 34 are not necessarily in fluid communication with a cartridge and a transdermal delivery system as illustrated. Fluid sources of various configurations may be connected to the inlet port, and fluid delivery systems of various configurations may be connected to the outlet port, while benefitting from the advantages of the pump system according to embodiments of this invention.

The valve piston 28 comprises sealing 46 engaging the inner surface 23 of the pump housing 22. The valve piston 28 and the pump piston 26 may be produced by various molding and other manufacturing techniques. For instance, the sealings may be separately formed (e.g. O-rings) from the pistons and assembled thereto, or form an integral part of the pistons, for example manufactured by two component injection molding.

The pump piston 26 and the valve piston 28 are coupled via respective first and second transmissions 52, 54 to the pump drive 16. In the illustrated exemplary embodiment, the transmissions comprise a first and a second toothed rack 40, 48 fixed to respectively the pump piston 26, and the valve piston 28, engaging a pinion gear 50, 42 of a reduction gear chain coupled to the pump drive 16.

Advantageously, as best seen in FIG. 2, the pump drive 16 comprises a valve motor 31 coupled via a first transmission 52 to the valve piston, and a piston motor 30 coupled to the pump piston 26 via a second transmission 54. The piston and the valve motors 30, 31 are configured to drive the pump piston and the valve piston independently from each other. Each motor has two phases and comprises a first coil 30a, 31a and a second coil 30b, 31b. According to this driving configuration, the volume to be pumped may advantageously be adjusted for delivering an accurate volume of a drug according to a variable dose setting. This may be particularly advantageous for instance for accurately completing a bolus administration of a drug.

The pump drive 16 may be operated by the control system 12 in order to impart an axial displacement of the valve piston 28 relative to the pump piston 26 in order to vary the stroke length of the pump piston thereby adjusting the volume of the pump chamber as required.

Although, reduction gears and racks have been described for the transmissions between the motors and the pistons, it will be appreciated that other forms of transmissions may be used according to other embodiments of the invention to couple the drive motors to the pistons, including worm gears, belt drive transmissions and linear actuators, that are per se known drive and transmission systems.

Figure 5D:
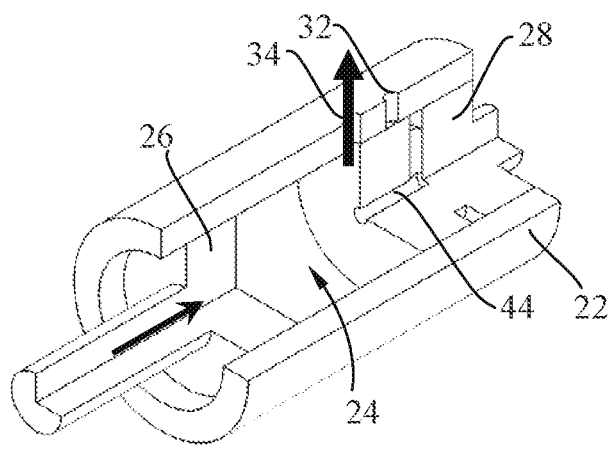

Referring in particular to FIGS. 5a to 5e, a pumping cycle according to an embodiment of the invention is illustrated. At the beginning of a pump chamber filling step, as best seen in FIG. 5a, the valve piston 28 is adjacent the pump piston 26, with the pump chamber 24 at essentially zero volume. The valve channel 44 is aligned with the inlet port 32 of the pump housing 22 while the outlet port 34 is sealed by sealings 46b, 46c located around the circumference of the valve piston 28. It may be noted, in a variant, that the sealing could also be shaped to circumscribe the outlet 34 without encircling the valve piston.

In a pump chamber filling step, as best seen in FIG. 5b, the pump piston 26 is driven away from the valve piston 28 which remains fixed inside the pump housing 22. Fluid is therefore drawn from the inlet port 32 through the valve channel 44 into the pump chamber 24.

Upon completion of the piston chamber filling stroke, both pump piston 26 and valve piston 28 are driven in the same axial direction, over the same distance, as illustrated in FIG. 5c to open the outlet port 34 and close the inlet port 32. This is done by moving the valve piston 28 away from the outlet port 34 such that the outlet port is in fluid communication with the pump chamber, and moving the valve channel 44 out of alignment with the inlet port 32. Sealing 46c between the valve piston and pump chamber housing inner surface 23 prevents liquid in the pump chamber from communicating with the inlet channel.

Figure 5E:
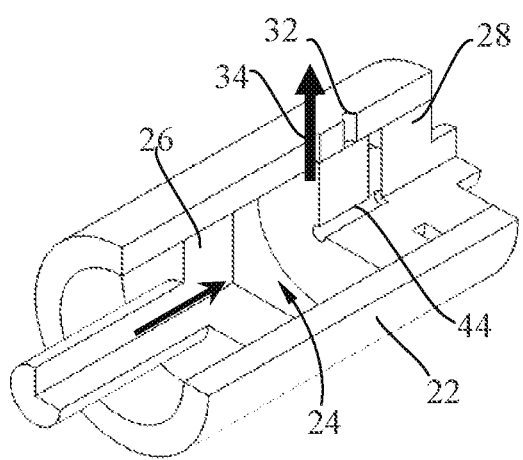

The pump piston 26 is then moved towards the valve piston 28 to expel the fluid from the pump chamber 24 through the outlet port 34 as shown in FIGS. 5d and 5e, during a drug administration phase.

When a new or subsequent pump cycle is needed, after the end of the pump chamber emptying phase, the valve piston 28 and pump piston are driven back to the fill start position as illustrated in FIG. 5a.

Because the pump piston and the valve piston are moved in the same direction prior to expulsion of the liquid from the pump chamber, and then also in the same opposite direction when moving from the end of expulsion step to the beginning of a new filling step, any play (tolerances) in the transmissions between the respective pistons and motors are taken up before the pump chamber filling and before the pump chamber emptying, thus reducing an alteration of the pumped volume due to possible back-lash occurring when driving the pump piston and the valve piston. Also, the volume of liquid to be pumped may be varied by varying the stroke of the pump piston 26. The pump has therefore the advantage of delivering precise adjustable volumes of a drug in a compact and simple configuration. Moreover, the pump configuration according to the invention is well suited for applications that require low energy consumption. Also, the valve piston 28 may be adjusted in several axial safety positions (see in particular FIGS. 6e, 6l and 7d) in order to prevent any fluid communication between the pump chamber 24 and any ports 32, 34 of the pump housing 22 during axial displacement of the valve piston 28. The valve piston 28 is further configured to allow fluid communication between the pump chamber 24 and only one port of the pump as a function of the axial position of the valve piston.

Figure 6A:
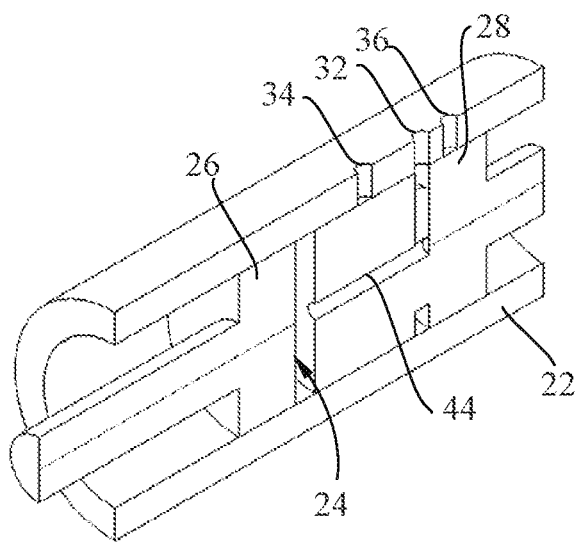
Figure 6B:
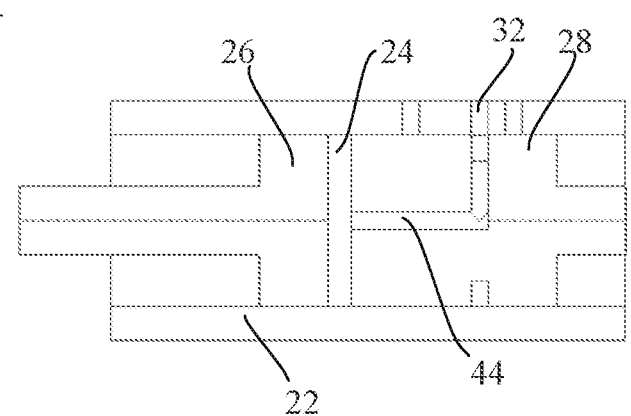
Figure 6J:
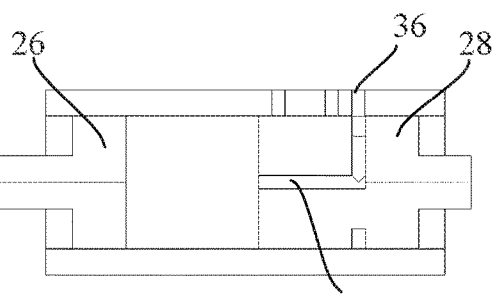
Figure 6K:
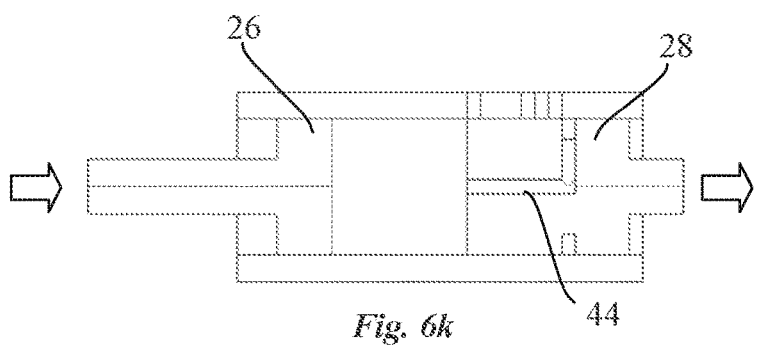
Figure 6L:
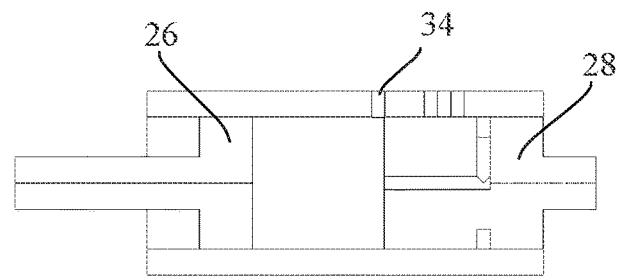
Figure 6M:
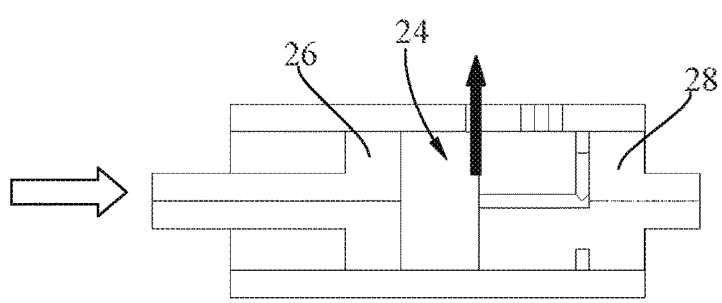
Figure 6N:
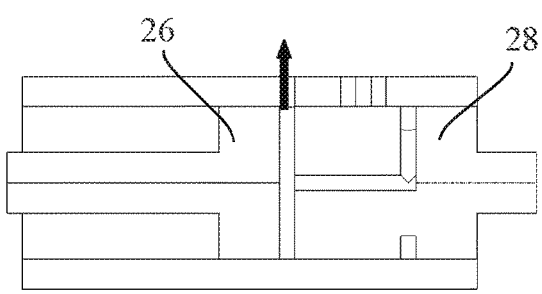

The driving configuration of this pump is also well suited for a drug reconstitution device according to another embodiment of the invention as shown in FIGS. 6a to 6n. The structure of the pump 14 is similar to the pump which has just been described. The inlet port of the pump housing 22 is however replaced by two drug reconstitution ports. More specifically, the drug reconstitution device may comprise a pump as shown in particular in FIG. 6a comprising a pump housing 22 provided with two drug reconstitution ports 32, 36 and an outlet port 34, and a docking interface (not shown) configured for coupling a first and a second constituent container containing respectively a solvent or diluent and an active substance which may be preferably in the form of a lyophilized substance. The docking interface may comprise a first and a second container docking interface configured to interconnect the first and second constituent containers respectively with the first and second drug reconstitution ports 32, 36 of the pump 14 in a fluidic manner through respectively a first and a second channel in order to dissolve the lyophilized substance so as to reconstitute a drug inside the second constituent container in a suitable form to be pumped into the pump chamber 24 and expelled through the outlet port 34 for administration to a patient.

In advantageous embodiment, the drug reconstitution device may replace the cartridge 4 in the patch pump 2 with the outlet port 34 of the pump connected to the transdermal delivery system 10 through a liquid conduit, for instance in the form of a tube for administering the reconstituted drug to a patient. The drug reconstitution device is however not necessarily integrated into a patch pump and may for example be incorporated in any type of fluid delivery device according to embodiments of this invention. The reconstituted drug may also be administered to a patient through an infusion tube connected to the outlet port 34 of the pump while benefitting from the advantages of the pump system according to embodiments of this invention.

Referring now in particular to FIGS. 6b to 6n, a pumping cycle of the pump of the drug reconstitution device according to an embodiment of the invention is illustrated. At the beginning of a pump chamber filling step, as illustrated in FIG. 6b the valve piston 28 is adjacent the pump piston 26, with the pump chamber 24 at essentially zero volume. The valve channel 44 is aligned with the first drug reconstitution port 32 of the pump while the second drug reconstitution port 36 and the outlet port 34 are sealed by customized sealings located of the valve piston 28.

In a pump chamber filling step, as best seen in FIG. 6c, the pump piston 26 is driven away from the valve piston 28 which remains fixed inside the pump housing 22. Solvent or diluent is therefore drawn from the first container through successively the first channel of the docking interface, the first drug reconstitution port 32, the valve channel 44 into the pump chamber 24.

Upon completion of the piston chamber filling stroke (FIG. 6d), both pump piston 26 and valve piston 28 are driven in the same axial direction, over the same distance, as illustrated in FIG. 6e in order to align the valve channel 44 with the second drug reconstitution port 36 (figure f) to bring the second container in fluid communication with the pump chamber 24 and to seal the first drug reconstitution port 32 and the outlet port 34 by the sealings located on the valve piston 28.

The pump piston 26 is then moved towards the valve piston 28, as shown in FIG. 6g, to expel the fluid from the pump chamber 24 through the valve channel 44, the second drug reconstitution port 36, the second channel of the docking interface into the second container to dissolve the lyophilized drug inside the second container during a drug reconstitution phase.

Upon completion of the piston drug reconstitution stroke (figure h), the pump piston 26 is driven away from the valve piston 28 which remains fixed inside the pump housing 22, as illustrated in FIG. 6i. The reconstituted drug is therefore drawn from the second container through the second channel of the docking interface, the second drug reconstitution port 36, the valve channel 44 into the pump chamber 24 during a chamber filling step.

Upon completion of the piston chamber filling stroke (FIG. 6j), both pump piston 26 and valve piston 28 are driven in the same axial direction, over the same distance, as illustrated in FIG. 6k, to open the outlet port 34 and close the second drug reconstitution port 36 while the first reconstitution port 32 remains close (FIG. 6l).

The pump piston 26 is then moved towards the valve piston 28 to expel the reconstituted drug from the pump chamber 24 through the outlet port 34 as shown in FIGS. 6m and 6n, during a drug administration phase.

In an advantageous embodiment, the pump is configured for automated drug reconstitution according to successive steps of a pumping sequence as shown in FIGS. 7a to 7g.

The first and second drug reconstitution ports 32, 36 of the pump housing 22 may for example be connected to respectively a first and a second container (not shown) containing respectively a pressurized solvent or diluent and an active substance which may be in the form of a lyophilized drug. During a drug reconstitution phase, as illustrated in FIG. 7a, the valve piston 28 is adjacent the pump piston 26. The valve channel 44 of the valve piston 28 is aligned with the first drug reconstitution port 32 of the pump and the second drug reconstitution port 36 is in fluid communication with the second container such that the pressurized solvent or diluent is urged from the first container successively through the first reconstitution port 32, the valve channel 44, the pump chamber 24, and the second drug reconstitution port 36 into the second container in which the diluent dissolves the active substance to reconstitute a drug inside the second container in a suitable form to be administered to a patient.

In a pump chamber filling step, as illustrated in FIG. 7b, the pump piston 26 is driven away from the valve piston 28 which remains fixed inside the pump housing 22. The reconstituted drug is drawn from the second container through the second drug reconstitution port 36 into the pump chamber 24. The pump chamber filling step is preferably initiated after the whole content of the first container has been emptied so that no more solvent is drawn into the pump chamber in the course of this step. An anti-backflow valve may however be mounted on the first drug reconstitution port 32 for safety reasons.

Upon completion of the piston chamber filling stroke (FIG. 7c), both pump piston 26 and valve piston 28 are driven in the same axial direction, over the same distance, as illustrated in FIG. 7d, in order to align the valve channel 44 with the outlet port 34 (FIG. 7e) and to close the first and second drug reconstitution ports 32, 36 by the sealings located on the valve piston 28.

The pump piston 26 is then moved towards the valve piston 28 to expel the reconstituted drug from the pump chamber 24 through the valve channel 44 and the outlet port 34 as shown in FIGS. 7f and 7g, during a drug administration phase The pump system configuration advantageously requires only two strokes of the pump piston according to the above described sequence of a drug reconstitution process, thereby allowing fast drug reconstitution with low power consumption.

In a variant, the solvent/diluent may be injected by a syringe by piercing a septum arranged in the inlet port and pushing the plunger of the syringe to urge the solvent/diluent into the second container, whereupon the valve system is operated as described above.

Figure 8:
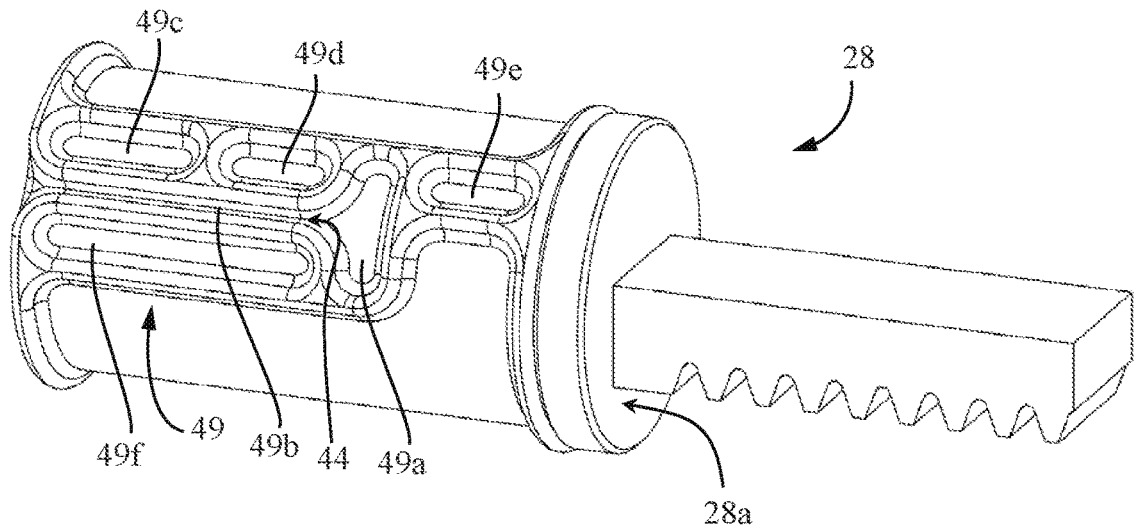
FIG. 8 is a perspective view of a valve piston according to another embodiment of the invention.

In an advantageous embodiment as illustrated in FIG. 8, the valve piston 28 comprises an over-molded part 49 over a portion of an outer surface of a valve piston core 28a. The over-molded part 49 comprises sealing beads configured to engage the inner surface 23 of the pump housing 22 (FIG. 9a) so as to form the valve channel 44 configured to selectively connect and disconnect ports 32, 34 to the pump chamber 24 of a pump suitable for a drug reconstitution device or for delivery of drugs from multiple drug containers. The valve channel 44 extends from the pump chamber 24 to ports 32, 34 depending on the axial position of the valve piston.

More particularly, the over-molded part 49 comprises a valve channel portion 49a, 49b which is surrounded by a sealing bead that engages the inner surface 23 of the pump housing 22 in order to form the valve channel 44. The valve channel portion 49a, 49b comprises a valve recess 49a and a valve groove 49b in fluid communication with the valve recess 49a and the pump chamber 24. The valve recess 49a extends circumferentially over a certain angular distance in order to be in fluid communication with port 32 or port 34 of the pump as a function of the axial position of the valve piston 28. The over-molded part 49 comprises additional recesses 49c, 49d, 49e, 49f surrounded by sealing beads arranged around the valve channel portion 49a, 49 which advantageously selectively seals at least two ports according to the pumping sequence of the pump with a minimum of friction between the inner surface 23 of the pump housing 22 and the over-molded part 49, when the latter is actuated in translation.

The over-molded part 49 of the valve piston 28 may be made from a soft component such as a thermoplastic elastomer (TPE) or a silicon rubber in order to achieve the function of sealing between port 32, port 34, port 36 and the valve channel which is in fluid communication with the pump chamber 24. The valve piston 28 according to this embodiment advantageously reduces the number of components in contact with the pumped fluid, since the valve channel and the sealing are made from the same material, thereby reducing the risk of generating particles within the pump. It also facilitates achieving conformity with drug compatibility by reducing the number of materials to be tested. Moreover, the dimension tolerance of the valve piston core 28a may be increased without adverse effect on the sealing properties of the pump thereby easing the production process.

Figure 9A:
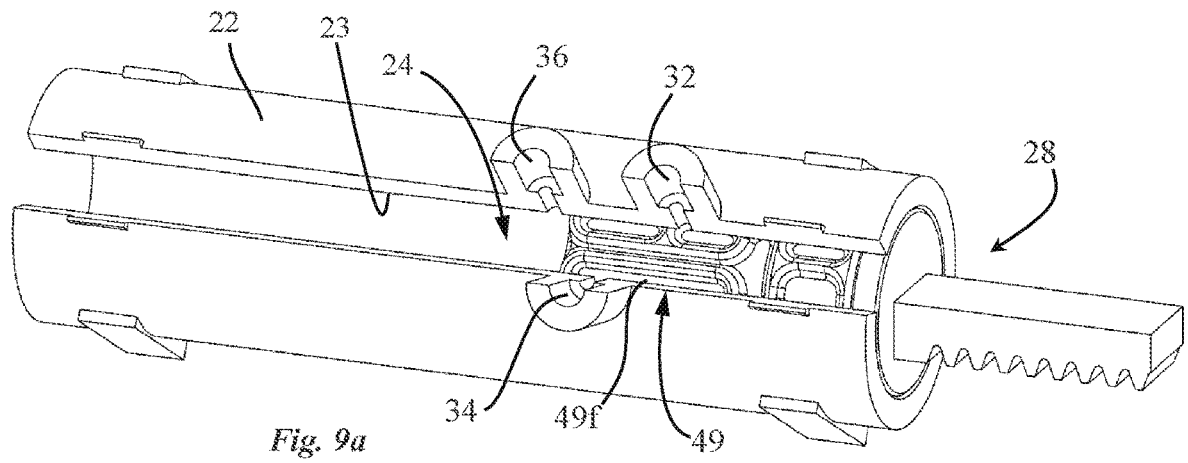
FIGS. 9a to 9e are perspective partial cross-sectional views of a pump system comprising the valve piston of FIG. 8, showing the valve piston in different axial positions.

As illustrated in FIG. 9a, the pump chamber 24 is sealed from both port 32 and port 34 by the over-molded part 49 and is in fluid communication with port 36. Fluid may therefore be pumped from port 36 directly into the pump chamber 24 or expelled from the pump chamber 24 through port 36 depending on the pumping sequence and the pump configuration.

Figure 9B:
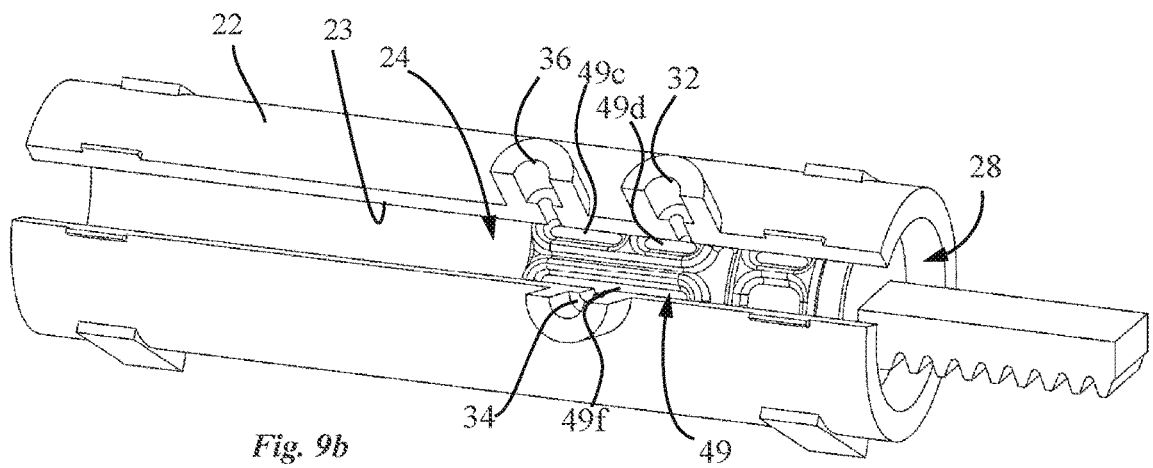

Axial displacement of the valve piston 28 towards the pump piston (not shown) brings the pump in a safety configuration in which all the ports 32, 34, 36 are sealed from the pump chamber 24 by respective sealing rings surrounding (forming) the recesses 49d, 49f and 49c of the over-molded part 49 (FIG. 8) as illustrated in FIG. 9b.

Figure 9C:
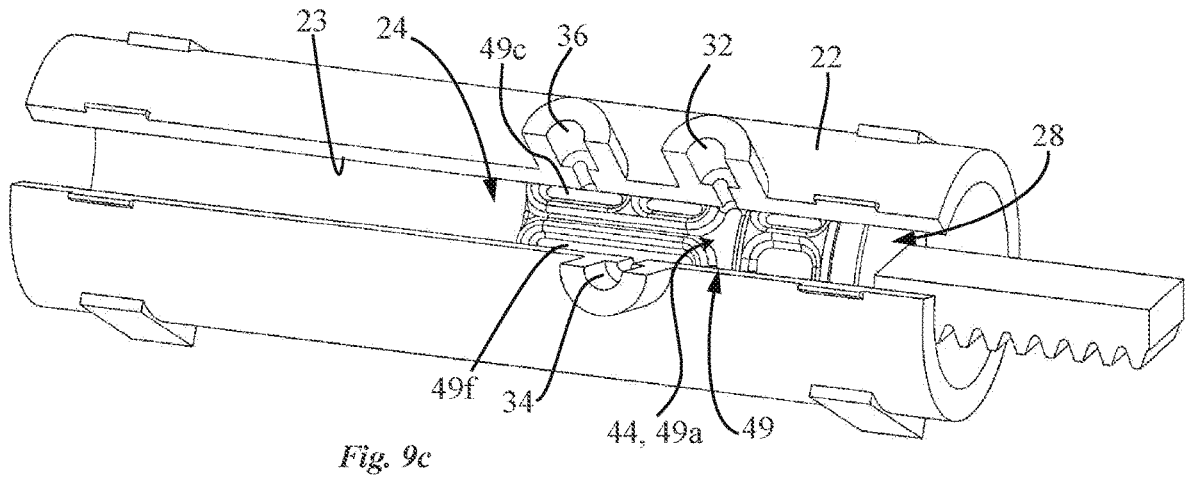

Further axial displacement of the valve piston 28 towards the pump piston (not shown) brings port 32 in fluid communication with the pump chamber 24 through the valve channel portion 49a, 49b, whereby the other ports 34, 36 are sealed from the pump chamber 24 by sealing rings surrounding forming the recesses 49f and 49c of the over-molded part 49 as illustrated in FIG. 9c. Fluid may therefore be pumped from port 32 through the valve channel (not shown) and into the pump chamber 24 or expelled from the pump chamber 24 through the valve channel and port 32 depending on the pumping sequence and the pump configuration.

Figure 9D:
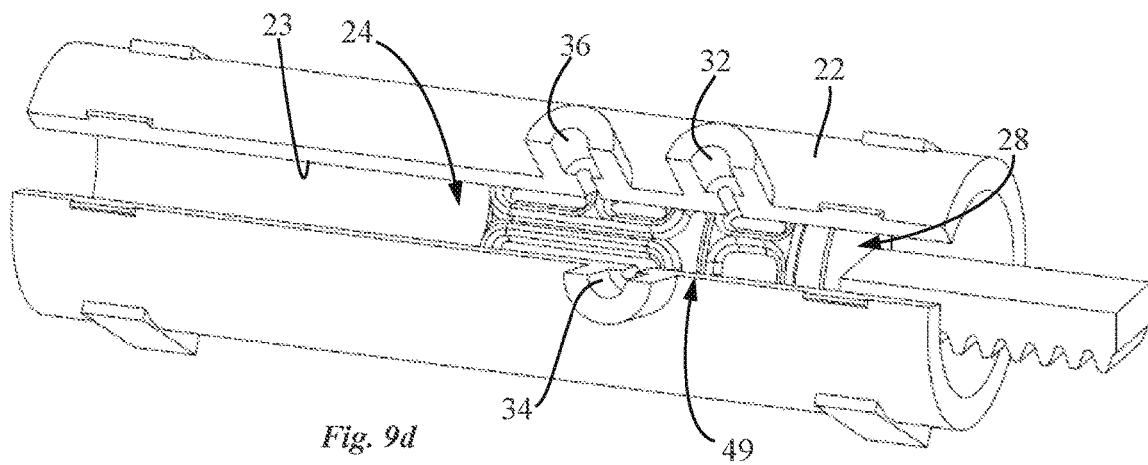
Figure 9E:
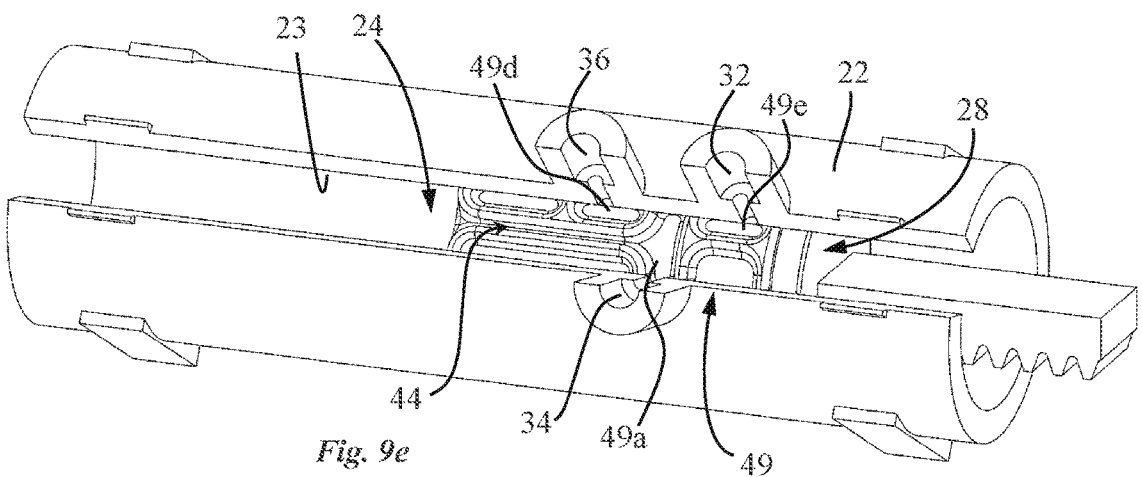

Even further axial displacement of the valve piston 28 towards the pump piston (not shown) brings the pump first in a safety configuration (FIG. 9d) in which all the ports 32, 34, 36 are sealed from the pump chamber 24 by respective sealing rings surrounding the recesses 49e, 49f and 49d of the over-molded part 49 and then in a configuration (FIG. 9e) in which port 34 is in fluid communication with the pump chamber 24 through the valve channel portion 49a, 49b, whereby ports 32, 36 are sealed from the pump chamber 24 by respective sealing rings around recesses 49e and 49d of the over-molded part 49.

Any of ports 32, 34, 36 of the pump may function as an inlet port or an outlet port according to the configuration of the pump. There may also be provided a greater plurality of ports, for instance four, five, six or more ports. Ports may be connected to constituents of a drug to be reconstituted, for instance a powdered drug and a solvent, or to two or more liquid drugs, or to a combination of drug constituents for reconstitution and liquid drugs. Multi drug therapy can thus be administered by drawing in a liquid drug in the pump chamber from a first port connected to a first drug recipient, moving the valve piston to align the valve channel 44, 49*a*, 49*b* with an outlet port 34 and expelling the first drug, then repeating the operation with a second drug in a second container connected to a second inlet port, for sequential delivery of drugs. Further drugs can be connected to third or more ports and be delivered in a similar manner. It may also be possible to mix two or more drugs in the pump chamber by sequential drawing in of the two or more drugs, the valve piston being moved between intake strokes of the pump piston from one port connected to a first drug to another port connected to another drug, before then moving the valve piston to the outlet port for the expel phase.

The connection of two or more drug containers to respective two or more inlet ports may also serve to provide an increased volume of medicament in the medical device. For instance patient's with greater body weight may require higher volumes of a drug in a delivery device, which may be provided by connecting more than one drug container to the drug delivery device.

In an embodiment, the over-molded part 49 may be modified to perform the function of sealing between the inlet/outlet ports and the valve channel for a pump of the type illustrated in FIGS. 5*a* to 5*e*.

Referring now to FIGS. 10*a* to 10*d*, the transdermal delivery system 10 according to another embodiment of the invention, comprises a needle actuation mechanism and a needle guiding element 20 for axial displacement of a needle and a cannula. The needle actuation mechanism comprises a cam member 56 rotatable relative to the needle guiding element 20. The cam member 56 has a cam housing 58, which may for instance be generally cylindrical, and which comprises a bearing shaft receiving portion 66 for rotation of the cam member 56 around a bearing shaft 67 and an annular compartment 68 lodging a biased element 60 preferably in the form of a preloaded torsion spring configured to impart rotational movement to the cam member 56. The bearing shaft may be fixed to a base and/or cover of the patch pump housing. Other rotation guide configurations may however be implemented. For instance, the cam housing may comprise an integral shaft at axial ends thereof that engage in bearing cavities formed in or fixed to a base and/or cover of the patch pump.

Figure 10A:
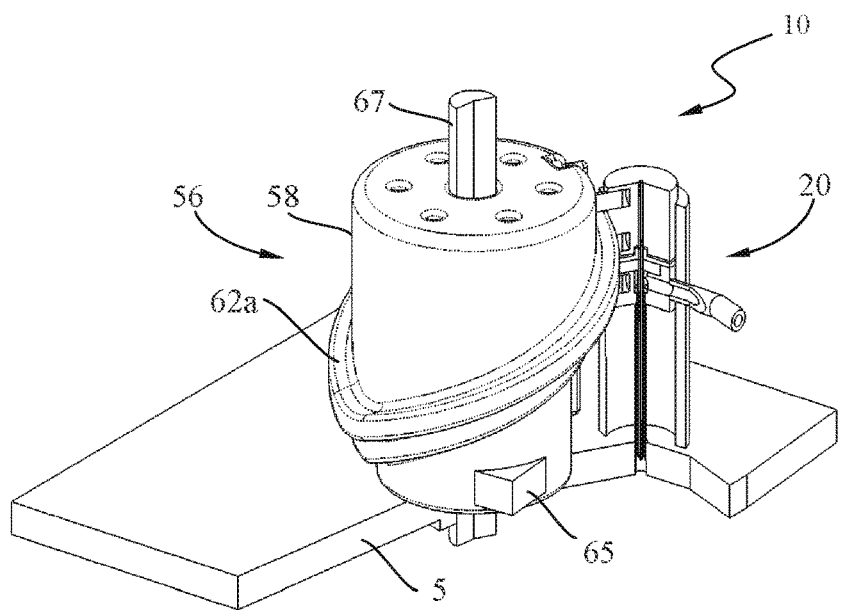
FIGS. 10a to 10c are perspective and partial cross-sectional views of a transdermal delivery system of a drug delivery device, according to an embodiment of the invention.
Figure 10B:
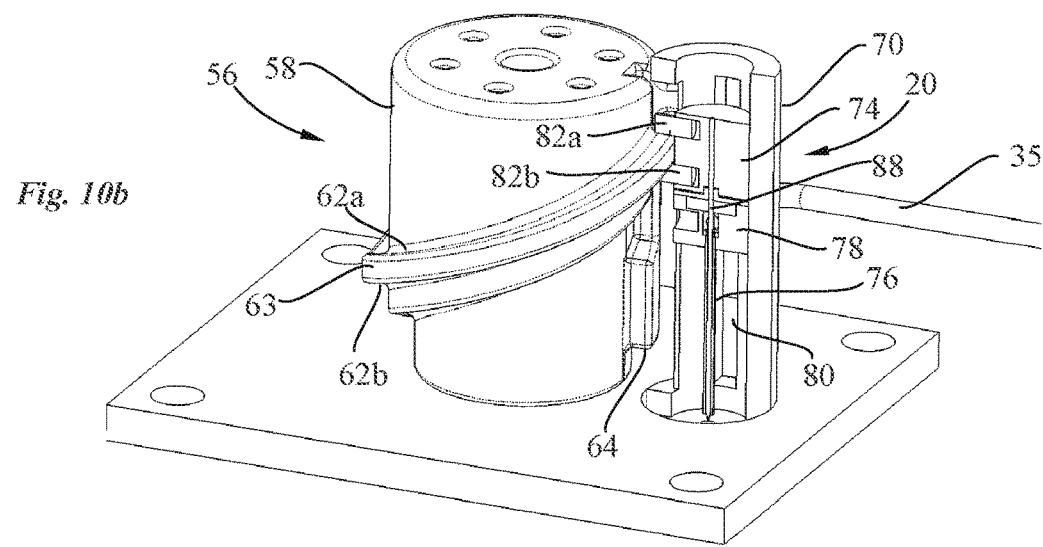
Figure 10C:
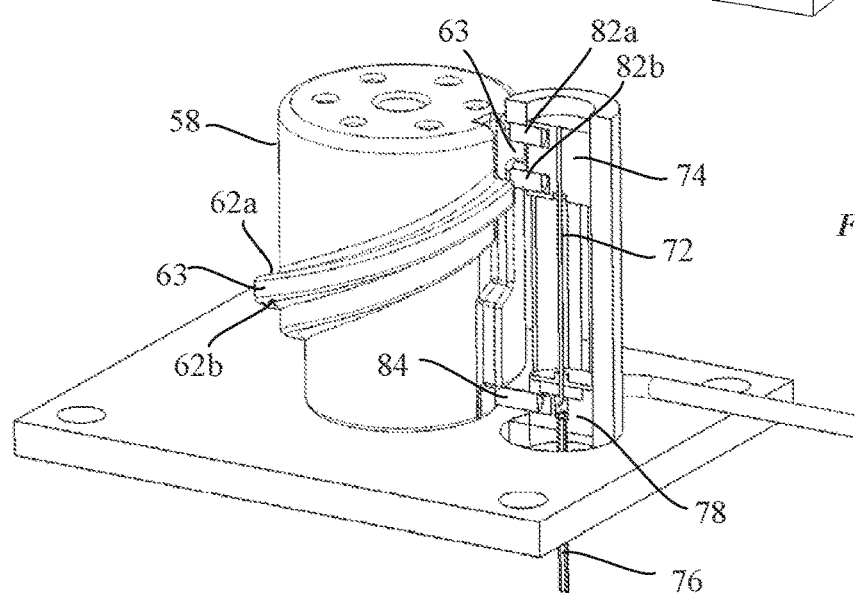

The cam member 56 comprises a cam locking portion 65, as illustrated in particular in FIG. 10*a*, which may be in the form of a land portion provided on the lower part of the cam housing 58 to engage a cam engaging element to prevent rotation of the cam member prior to use of the patch pump 2. The cam engaging element may be in the form of a rod 47, as shown in FIG. 13*a*, with one end thereof abutting against the land portion of the cam housing while the other end of the rod is connected to the valve piston. A needle insertion release mechanism is operated by the control system 12, upon actuation of the button 3*c* provided on the cover portion 3 of the patch pump 2, which drives the valve motor 31 in order to move the valve piston 28 away from the cam housing thereby disengaging the rod 47 from the land portion 65 as shown in FIG. 13*b*. Other cam engaging configurations may however be envisaged. The end of the rod 47 may for instance be lodged inside an aperture formed in the cam housing.

In a variant, the needle insertion release mechanism may be manually operated. For instance, the cam engaging element may protrude from an orifice formed on the patch pump housing and may be mounted on a spring to translate between a first axial position in which the came engaging element block the rotation of the cam member and a second axial position in which the came engaging element is disengaged from the cam member.

FIG. 12*a* shows the transdermal delivery system 10 prior to use. The needle 72 and the cannula 76 are in a retracted position. The guiding element 20 is preferably in the form of a cylindrical housing 70 which contains a needle 72 and a cannula 76 connected respectively to a cylindrical needle holder 74 mounted on top of a cylindrical cannula holder 78. The needle holder 74 comprises engagement portions 82*a*, 82*b*, preferably in the form of projecting parts extending perpendicularly to the needle/cannula axis to engage with a first and a second cam surfaces 62*a*, 62*b* provided on each side of a needle holder guide 63, which is in the form of a protruding part, disposed around the circumference of the cam housing 58 of the cam member 56. The cannula holder 78 comprises a locking portion 84, for instance in the form of a projection extending transversely to the needle/cannula axis, configured to engage a complementary locking portion, for instance a locking shoulder 64 provided on a lower part of the cam member 56 and disposed around a part of the circumference of the cam housing 58.

The needle guide 63 and locking surface 64 are arranged around the circumference of the cylindrical housing 58 of the cam member 56 such that the needle 72 and the cannula 76 are moved together between a retracted position and an extended position upon rotation of the cam member 56 through a predetermined angle and such that the needle 72 is brought back in the retracted position upon further rotation of the cam member 56 while the locking portion 84 of the cannula holder 78 abuts against the locking surface 64 to maintain the cannula in the extended position. The axial insertion of the cannula 76 is therefore imparted by the movement of the needle holder 74, driven by the needle guide, which pushes the cannula holder 78 downwards during insertion of the needle 72, whereupon the locking portion 84 of the cannula holder 78 abuts against the locking surface 64 to securely maintain the cannula 76 in the extended position.

The needle holder guide 63 is preferably arranged around the circumference of the cam housing 58 along a first portion with a downward insertion gradient followed by a second portion with an upward retraction gradient as to form an inclined protruding part which resembles an ellipse in order to impart to the needle 72 the above described movements. However, it will be appreciated that the needle holder guide 63 may follow a slightly different trajectory to achieve the same function. For example, the gradient of the first and second portions of the inclined protruding part may be higher or lower in order to control the velocity of insertion and/or velocity of retraction of the needle optimally as needed for the comfort of use and reliability of transdermal cannula placement.

The needle actuation mechanism has the advantage to impart an axial insertion and retraction movement to the needle 72 through a rotation of the cam housing 58 that may be less than 360°, or in a variant (not shown), more than 360°.

In a variant (not shown), the protruding part of the needle holder guide 63 may be replaced by a corresponding groove, configured to receive a projecting part of the needle holder in order to achieve the same function.

According to an alternative embodiment of the invention (not shown), the transdermal delivery system is configured for insertion of a needle without the use of a cannula. In this alternative embodiment, rotation of the cam housing is stopped by a locking element when the needle has reached the extended position. Upon completion of the drug injection, the needle insertion release mechanism is used to disengage the locking element from the cam housing to enable further rotation of the cam housing to safely move the needle in the retracted position thereby avoiding needle injury.

As best seen in FIGS. 11a and 12b, the cannula holder 78 comprises a through-hole 88 for receiving the needle 72 and comprises an inlet aperture 86 for receiving an inlet tube 35 corresponding to the second conduit connected to the outlet port of the pump described above. The needle housing 70 of the needle guiding element 20 comprises a vertical groove 80 (FIG. 10b) for accommodating a part of the inlet tube 35 when the cannula holder 78 is moved along its axis. Advantageously, the needle 72 performs the function of sealing so as to avoid any leakage prior to use of the patch pump. To this end, the cannula holder 78 comprises an inlet channel 87 extending from the inlet aperture 86 to the through-hole 88. Accordingly, the inlet aperture 86 of the cannula holder 78 is configured to be in fluid communication with the cannula 76 once the needle 72 is moved back in the retracted position (FIG. 10e) after actuation of the transdermal delivery system.

With reference to FIGS. 12a to 12e, the working principle of the transdermal delivery system according to an embodiment of the invention will now be described.

FIG. 12a shows the transdermal delivery system 10 prior to use. The needle 72 and the cannula 76 are in a retracted position. Upon actuation of the needle insertion release mechanism, the cam housing 58 of the cam member 56 rotates in a spring biased direction (counterclockwise in the illustration of FIG. 12b) thereby imparting a downward movement to the needle holder 74 and the cannula holder 78 in order to move the needle 72 and the cannula 76 in the extended position.

FIG. 12c shows the transdermal delivery system 10 when both the needle 72 and the cannula 76 are transdermally inserted after a rotation of approximately 180° of the cam housing 58. It may be noted that the needle holder guide 63 may be configured with a different profile such that full needle insertion is achieved with a rotation of less than 180°, or conversely with a rotation of more than 180°. In a variant, the needle holder guide at its end of travel section may spiral above the start position to allow the cam housing to rotate around more than 360°.

FIG. 12d shows the transdermal delivery system 10 after further rotation of the cam housing 58 in which the locking portion 84 of the cannula holder 78 abuts against the locking surface 64 thereby securing the cannula 76 in the extended position. Further rotation of the cam housing 58 moves the needle holder 74 engaging with needle holder guide 63 upwards in order to bring the needle 72 in the retracted position, whereupon the inlet tube 35 is no longer sealed allowing the injection of a drug as shown in FIGS. 11b and 12e.

The above described transdermal delivery system is configured to work with a needle diameter of 0.2 mm and a cannula diameter of 0.4 mm for the injection of standard viscosity drug (up to 10 cST) thereby reducing patient's discomfort.

For applications requiring high viscous drugs, the transdermal delivery system can be adapted with a higher fluid path diameter in order to allow the injection with low pressure losses between the pump and the end of the needle.

While this invention has been described with reference to several embodiments, it should be appreciated that some changes may be brought to the invention without departing from the scope of the invention. For instance, the arrangement of the inlet port, the outlet port and, if applicable, the drug reconstitution port(s) of the pump, as illustrated according to several embodiments of the invention, may be interchanged and/or the flow direction may be reversed according to the application.

LIST OF REFERENCED FEATURES

Drug delivery device
  Patch pump 2
    Patch pump housing
      Cover 3
        Activation button 3c
        Status display 3d
      Base 5
        Skin bonding surface 5b
    Drug cartridge 4
    Power source (battery) 6
    Pump system
      Pump 14
        Pump housing 22
        housing inner surface 23
        Ports 32, 34, 36
        Inlet/first drug reconstitution port 32
        outlet port 34
        second drug reconstitution port 36
        inner surface 23
      Pump chamber 24
      Pump piston 26
        Sealing 38
        o-ring
      Valve piston 28
        Valve piston core 28a
        lateral guide surface 25
        chamber side face 27
        Valve channel 44
        first portion 44a
        second portion 44b
        Sealing 46, 46a, 46b, 46c
        Over-molded part 49
        Valve channel portions 49a, 49b
        Valve recess 49a
        Valve groove 49b
        Recesses 49c, 49d, 49e, 49f
        first conduit 33
        second conduit 35
      Pump drive 16
        Piston motor 30
        Two coils 30a, 30b
        Valve motor 31
        Two coils 31a, 31b
        Transmission 52, 54
        Toothed rack 40, 48
        reduction gear train 53
        pinion 42, 50
        cam engaging element 47
        rod
  Transdermal delivery system 10
    Needle/cannula actuation mechanism
      Cam member 56
      Cam housing 58

Cylindrical housing
  Shaft receiving portion 66
  Bearing shaft 67
  Annular compartment 68
  Biased element 60
  Preloaded torsion spring
  Needle cam surfaces 62*a*, 62*b*
  Needle holder guide 63
  Cannula locking surface 64
  Needle insertion release mechanism 65
  Cam locking portion
Needle/cannula guiding element 20
  Needle housing 70
  Vertical groove 80
Needle 72
  Needle holder 74
  Cam engaging portions
  Projecting parts 82*a*, 82*b*
Cannula 76
  Cannula holder 78
  Cam engaging portion 84
  Inlet aperture 86
  Inlet channel 87
  Needle receiving means 88
  Through hole
  Inlet tube 35
Control system 12
  Electronic circuit board 90

The invention claimed is:

1. A pump system for a drug delivery device, the pump system comprising a pump drive and a pump having a pump housing comprising an inlet port and an outlet port and forming a pump chamber containing a pump piston and a valve piston, wherein the pump comprises a valve channel configured to selectively connect and disconnect at least one of the inlet and outlet ports of the pump housing to the pump chamber as a function of a position of the valve piston, wherein the pump piston and the valve piston are linearly slidable along a common axis within the pump chamber, wherein the valve piston and the pump piston are independently actuated, wherein the valve piston comprises an over-molded part comprising a valve channel portion configured to engage an inner surface of the pump housing so as to form the valve channel with said inner surface, and wherein the over-molded part is configured to selectively seal the inlet and outlet ports from the pump chamber.

2. The pump system according to claim 1, wherein the pump drive comprises a valve motor coupled to the valve piston and a piston motor coupled to the pump piston, the valve and piston motors being independently controllable.

3. The pump system according to claim 2, wherein the pump drive comprises a first transmission coupling the valve motor to the valve piston, and a second transmission coupling the pump motor to the pump piston.

4. The pump system according to claim 3, wherein each of the first and second transmissions comprise a toothed rack fixed to the respective piston, and a reduction gear assembly between the respective motor and toothed rack.

5. The pump system according to claim 1, wherein the pump drive is configured to linearly actuate the valve piston without any angular movement of the valve piston.

6. A drug reconstitution device including the pump system according to claim 1, wherein the pump housing comprises an additional port, said additional port and the inlet port corresponding to first and second drug reconstitution ports, wherein the drug reconstitution device is configured for coupling a first constituent container containing a first constituent and a second constituent container containing a second constituent, wherein the outlet port of the pump housing is configured to deliver a reconstituted drug comprising the first and second constituents.

7. The drug reconstitution device according to claim 6, wherein the over-molded part is configured to selectively seal the first and second drug reconstitution ports and the outlet port from the pump chamber.

8. A drug reconstitution device including a pump system, the pump system comprising a pump drive and a pump having a pump housing comprising an inlet port and an outlet port and forming a pump chamber containing a pump piston and a valve piston, wherein the pump comprises a valve channel configured to selectively connect and disconnect at least one of the inlet and outlet ports of the pump housing to the pump chamber as a function of a position of the valve piston, wherein the pump piston and the valve piston are linearly slidable along a common axis within the pump chamber, and wherein the valve piston and the pump piston are independently actuated, wherein the pump housing comprises an additional port, said additional port and the inlet port corresponding to first and second drug reconstitution ports, wherein the drug reconstitution device is configured for coupling a first constituent container containing a first constituent and a second constituent container containing a second constituent, wherein the outlet port of the pump housing is configured to deliver a reconstituted drug comprising the first and second constituents, the drug reconstitution device further comprising a docking interface comprising a first and a second container docking interface configured to interconnect the first and second constituent containers respectively with the first and second drug reconstitution ports of the pump housing in a fluidic manner.

9. A method for reconstituting a drug using a pump system comprising a pump drive and a pump having a pump housing, the pump housing comprising a first drug reconstitution port, a second drug reconstitution port and an outlet port, the pump housing forming a pump chamber containing a pump piston and a valve piston, wherein the pump comprises a valve channel configured to selectively connect and disconnect at least one of the first and second drug reconstitution ports to the pump chamber as a function of a position of the valve piston and wherein the valve piston and the pump piston are independently actuated, the method comprising the following steps:
  i) setting the valve piston in a first axial position in which the first and second drug reconstitution ports of the pump housing are in fluid communication;
  ii) urging a first constituent contained in a first container through the valve channel into a second container containing a second constituent in order to reconstitute the drug inside the second container during a drug reconstitution phase;
  iii) driving the pump piston away from the valve piston along a pump axis to draw the reconstituted drug from the second container into the pump chamber during a chamber filing phase;
  iv) driving the valve piston in a second axial position, upon completion of the chamber filling phase, in which the valve channel is aligned with the outlet port while the first and second drug reconstitution ports are closed by the valve piston; and
  v) driving the pump piston towards the valve piston along the pump axis to expel the reconstituted drug from the pump chamber, through the valve channel and the outlet port during a drug administration phase.

10. The method according to claim 9, wherein the valve piston is set in a safety position, prior to step i), in which the first and second drug reconstitution ports and the outlet port of the pump housing are closed by the valve piston.

11. The method according to claim 9, wherein the first container is pressurized thereby urging the solvent from the first container into the second container during the drug reconstitution phase without having the need to drive the pump system.

* * * * *